US012698316B2

(12) United States Patent
Mahon et al.

(10) Patent No.: US 12,698,316 B2
(45) Date of Patent: Aug. 4, 2026

(54) ENGINEERED IMMUNE-MOBILIZING T-CELL RECEPTORS WITH ENHANCED AFFINITY FOR HIV-1 GAG

(71) Applicant: IMMUNOCORE LIMITED, Abingdon (GB)

(72) Inventors: Tara Mahon, Abingdon (GB); Yi Li, Abingdon (GB)

(73) Assignee: IMMUNOCORE LIMITED, Abingdon (GB)

( * ) Notice: Subject to any disclaimer, the term of this patent is extended or adjusted under 35 U.S.C. 154(b) by 0 days.

(21) Appl. No.: 17/817,301

(22) Filed: Aug. 3, 2022

(65) Prior Publication Data

US 2023/0192806 A1 Jun. 22, 2023

Related U.S. Application Data

(63) Continuation of application No. 16/087,041, filed as application No. PCT/GB2017/050805 on Mar. 22, 2017, now Pat. No. 11,440,944.

(30) Foreign Application Priority Data

Jun. 23, 2016 (GB) ...................................... 1604953

(51) Int. Cl.

| | |
|---|---|
| *C07K 14/725* | (2006.01) |
| *C07K 14/705* | (2006.01) |
| *C07K 16/28* | (2006.01) |
| *A61K 38/00* | (2006.01) |
| *A61K 47/64* | (2017.01) |

(52) U.S. Cl.
CPC ...... *C07K 14/7051* (2013.01); *C07K 16/2809* (2013.01); *A61K 38/00* (2013.01); *A61K 47/6425* (2017.08); *C07K 2317/92* (2013.01); *C07K 2317/94* (2013.01); *C07K 2319/30* (2013.01)

(58) Field of Classification Search
CPC .................................................. C07K 14/7051
See application file for complete search history.

(56) References Cited

U.S. PATENT DOCUMENTS

| | | | |
|---|---|---|---|
| 8,378,074 B2 | 2/2013 | Jakobsen et al. | |
| 8,519,100 B2 | 8/2013 | Jakobsen et al. | |
| 9,068,178 B2 | 6/2015 | Jakobsen et al. | |
| 9,255,135 B2 | 2/2016 | Jakobsen et al. | |

FOREIGN PATENT DOCUMENTS

| | | |
|---|---|---|
| CN | 101155829 A | 4/2008 |
| CN | 104017067 A | 9/2014 |
| CN | 106478807 A | 3/2017 |
| JP | 2008-535826 A | 9/2008 |
| WO | WO 2005/113595 A2 | 12/2005 |
| WO | WO 2005/114215 A2 | 12/2005 |
| WO | WO 2006/103429 A2 | 10/2006 |
| WO | WO 2018/073595 A1 | 4/2018 |

OTHER PUBLICATIONS

Franchini, G., and M. L. Bosch, May 1989, Genetic Relatedness of the Human Immunodeficiency Viruses Type 1 and 2 (HIV-1, HIV-2) and the Simian Immunodeficiency Virus (SIV), Annals NY Acad. Sci. 554(1):81-87.*
Gao, F., et al., Jul. 1998, A Comprehensive Panel of Near-Full-Length Clones and Reference Sequences for Non-Subtype B Isolates of Human Immunodeficiency Virus Type 1, J. Virol. 72(7):5680-5698.*
Varela-Rohena, A., et al., Dec. 2008, Control of HIV-1 immune escape by CD8 T cells expressing enhanced T-cell receptor, Nat. Med. 14(12):1390-1395.*
Bennett, M. S., et al., 2010, Fine-tuning of T-cell receptor avidity to increase HIV epitope variant recognition by cytotoxic T lymphocytes, AIDS 24:2619-2628.*
Dunn, S. M., et al., 2006, Directed evolution of human T cell receptor CDR2 residues by phage display dramatically enhances affinity for cognate peptide-MHC without increasing apparent cross-reactivity, Protein Science 15:710-721.*
Holler, P. D., et al., May 2000, In vitro evolution of a T cell receptor with high affinity for peptide/MHC, PNAS 97(10):5387-5392.*
Bennett, M.S. et al., "Fine-tuning of T-cell receptor avidity to increase HIV epitope variant recognition by cytotoxic T lymphocytes," AIDS, vol. 24, No. 17, pp. 2619-2628.
Bragado et al., "Allelic polymorphism in the coding region of human TCR Cα gene and characterization of structural variability in the α chain constant domain," International Immunology, vol. 6, Issue 2, Feb. 1994, pp. 223-230.
Foote and Winter, "Antibody framework residues affecting the conformation of the hypervariable loops," *Journal of Molecular Biology,* vol. 224, Issue 2, Mar. 20, 1992, pp. 487-499, https://doi.org/10.1016/0022-2836(92)91010-M.
International Preliminary Report on Patentability, Chapter 1, Patent Cooperation Treaty Application No. PCT/GB2017/050805, Sep. 25, 2018, 6 pages.

(Continued)

*Primary Examiner* — Jeffrey S Parkin

(74) *Attorney, Agent, or Firm* — Fenwick & West LLP

(57) ABSTRACT

The present invention relates to T cell receptors (TCRs) which bind the HLA-A*02 restricted peptide SLYNTVATL (SEQ ID NO: 1) derived from the HIV Gag gene product, p17. Said TCRs comprise non-natural mutations within the alpha and/or beta variable domains relative to a native HIV TCR. The TCRs of the invention possess unexpectedly high affinity, specificity and sensitivity for a complex of SEQ ID NO: 1 and HLA-A*02, and drive a particularly potent T cell response. Such TCRs are particularly useful in the development of soluble immunotherapeutic reagents for the treatment of HIV infected individuals.

6 Claims, 8 Drawing Sheets

Specification includes a Sequence Listing.

(56)  References Cited

OTHER PUBLICATIONS

International Search Report and Written Opinion, PCT Application No. PCT/GB2017/050805, Jun. 21, 2017, 11 pages.

Rolland et al., "Broad and Gag-Biased HIV-1 Epitope Repertoires Are Associated with Lower Viral Loads," *PLoS One*, Jan. 2008, 3(1): e1424, 6 pages.

Rosenberg et al., "Adoptive cell transfer: a clinical path to effective cancer immunotherapy," Nature Reviews Cancer, Apr. 2008, 8(4):299-308.

Sewell et al., "Antagonism of cytotoxic T lymphocyte-mediated lysis by natural HIV-1 altered peptide ligands requires simultaneous presentation of agonist and antagonist peptides," *European Journal of Immunology*, Sep. 1997, vol. 27, Issue 9, pp. 2323-2329.

Varela-Rohena, A. et al., "Control of HIV-1 immune escape by CD8 T cells expressing enhanced T-cell receptor," *nature medicine*, Dec. 2008, vol. 14, No. 12, pp. 1390-1395.

Winter and Harris, "Humanized antibodies," Immunology Today, vol. 14, Issue 6, Jun. 1993, pp. 243-246, https://doi.org/10.1016/0167-5699(93)90039-N.

International Search Report and Written Opinion, PCT Application No. PCT/GB2023/054236, May 26, 2023, 16 pages.

Laugel, Bruno, et al., "Design of Soluble Recombinant T Cell Receptors for Antigen Targeting and T Cell Inhibition," *The Journal of Biological Chemistry*, vol. 280, Issue 3, Jan. 2005, pp. 1882-1892, DOI:https://doi.org/10.1074/jbc.M409427200.

Lefranc, M., et al., The T Cell Receptor FactsBook, TRAC and TRBC1, 2001, Academic Press, ISBN 0-12-441352-8, pp. 76-77 and 188-191.

Aggen, D. H., et al., "Identification and engineering of human variable regions that allow expression of stable single-chain T cell receptors," *Protein Engineering, Design & Selection*, vol. 24, Issue 4, Apr. 2011, pp. 361-372, https://doi.org/10.1093/protein/gzq113.

Schiffter, H. A., "Pharmaceutical Proteins—Structure, Stability, and Formulation," Reference Module in Biomedical Sciences, Comprehensive Biotechnology (Second Edition), vol. 5, 2011, pp. 521-541, https://doi.org/10.1016/B978-0-08-088504-9.00468-2.

Springer, I. et al., "Contribution of T Cell Receptor Alpha and Beta CDR3, MHC Typing, V and J Genes to Peptide Binding Prediction," Frontiers in Immunology, vol. 12, Apr. 2021, pp. 1-11.

* cited by examiner

Figure 1

SEQ ID No: 2 Amino acid sequence of the wild type alpha chain variable domain (residues 1 – 112). CDRs 1, 2 and 3 are underlined and correspond to SEQ ID NOs: 20, 21, and 22 respectively. The native alpha chain extracellular constant region is shown in italics

```
           10        20        30        40        50        60
           *         *         *         *         *         *
MQKEVEQNSGPLSVPEGAIASLNCTYSDRGSQSFFWYRQYSGKSPELIMFIYSNGDKEDGRF
           70        80        90       100       110       120
           *         *         *         *         *         *
TAQLNKASQYISLLIRDSKLSDSATYLCAVRTNSGYALNFGKGTSLLVTPHIQKPDPAVYQL
          130       140       150       160       170       180
           *         *         *         *         *         *
RDSKSSDKSVCLFTDFDSQTNVSQSKDSDVYITDKTVLDMRSMDFKSNSAVAWSNKSDFACA
          190       200
           *         *
NAFNNSIIPEDTFFPSPESS
```

SEQ ID No: 3 Amino acid sequence of the wild type beta chain variable domain (residues 1 – 113). CDRs 1, 2 and 3 are underlined and correspond to SEQ ID NOs: 23, 24, and 25 respectively. The native beta chain extracellular constant region is shown in italics.

```
           10        20        30        40        50        60
           *         *         *         *         *         *
MDAGVTQSPTHLIKTRGQQVTLRCSPKSGHDTVSWYQQALGQGPQFIFQYYEEEERQRGNFPD
           70        80        90       100       110       120
           *         *         *         *         *         *
RFSGHQFPNYSSELNVNALLLGDSALYLCASSDTVSYEQYFGPGTRLTVTEDLKNVFPPEVAV
          130       140       150       160       170       180
           *         *         *         *         *         *
FEPSEAEISHTQKATLVCLATGFYPDHVELSWWVNGKEVHSGVSTDPQPLKEQPALNDSRYCL
          190       200       210       220       230       240
           *         *         *         *         *         *
SSRLRVSATFWQNPRNHFRCQVQFYGLSENDEWTQDRAKPVTQIVSAEAWGRAD
```

Figure 2

SEQ ID NO: 4 Amino acid sequence of the soluble extracellular region of the wild type HIV TCR alpha chain. CDRs are underlined. The constant region is shown in italics and the non-native cysteine residue is shown in bold and underlined (at position 48 of constant region).

```
           10        20        30        40        50        60
            *         *         *         *         *         *
MQKEVEQNSGPLSVPEGAIASLNCTYSDRGSQSFFWYRQYSGKSPELIMFIYSNGDKEDGRF
           70        80        90       100       110       120
            *         *         *         *         *         *
TAQLNKASQYISLLIRDSKLSDSATYLCAVRTNSGYALNFGKGTSLLVTPHIQKPDPAVYQL
          130       140       150       160       170       180
            *         *         *         *         *         *
RDSKSSDKSVCLFTDFDSQTNVSQSKDSDVYITDKCVLDMRSMDFKSNSAVAWSNKSDFACA
          190       200
            *         *
NAFNNSIIPEDTFFPSPESS
```

SEQ ID NO: 5 Amino acid sequence of the soluble extracellular region of the wild type HIV TCR beta chain. CDRs are underlined. The constant region is shown in italics and the non-native cysteine residue is shown in bold and underlined (at position 57 of constant region). Additional non-native amino acids at position 75 and position 89 of the constant region are also shown in bold and underlined.

```
           10        20        30        40        50        60
            *         *         *         *         *         *
MDAGVTQSPTHLIKTRGQQVTLRCSPKSGHDTVSWYQQALGQGPQFIFQYYEEEERQRGNFPD
           70        80        90       100       110       120
            *         *         *         *         *         *
RFSGHQFPNYSSELNVNALLLGDSALYLCASSDTVSYEQYFGPGTRLTVTEDLKNVFPPEVAV
          130       140       150       160       170       180
            *         *         *         *         *         *
FEPSEAEISHTQKATLVCLATGFYPDHVELSWWVNGKEVHSGVCTDPQPLKEQPALNDSRYAL
          190       200       210       220       230       240
            *         *         *         *         *         *
SSRLRVSATFWQDPRNHFRCQVQFYGLSENDEWTQDRAKPVTQIVSAEAWGRAD
```

Figure 3

Amino acid sequences of mutated TCR alpha chain variable regions of the invention. In each case CDRs are underlined and mutations are in bold

SEQ ID No: 6 (a15 m121)

QKEVEQNSGPLSVPEGAIASLNCTYSSWEGQSFFWYRQYSGKSPELIMFLYADPDKED
GRFTAQLNKASQYISLLIRDSKLSDSATYLCAVRTNSGYALNFGKGTSLLVTP

SEQ ID No: 7 (a12 m134)

QKEVEQNSGPLSVPEGAIASLNCTYSSWEGQSFFWYRQYSGKSPELIMFIYSNGDKED
GRFTAQLNKASQYISLLIRDSKLSDSATYLCAVRTNSGYALNFGKGTSLLVTP

Figure 4

Amino acid sequences of mutated TCR beta chain variable regions of the invention. In each case CDRs are underlined and mutations are in bold

SEQ ID No: 8 (b26 m121 and m134)

DAGVTQSPTHLIKTRGQQVTLRCSPKSGHDTVSWYQQALGQGPQFIFQAVRGVERQRG
NFPDRFSGHQFPNYSSELNVNALLLGDSALYLCASSDTVSYEQYFGPGTRLTVT

Figure 5

Amino acid sequences of alpha chains of TCR-anti-CD3 fusions of the invention m121

SEQ ID No: 9 Alpha chain (comprising SEQ ID NO: 6 and the constant domain of SEQ ID NO: 4,the last 8 amino acids at the C terminus are optional). CDRs are underlined and mutations are shown in bold.

[A/Q] KEVEQNSGPLSVPEGAIASLNCTYSSWEGQSFFWYRQYSGKSPELIMFLYADPDKED
GRFTAQLNKASQYISLLIRDSKLSDSATYLCAVRTNSGYALNFGKGTSLLVTPHIQKPDPAVYQLR
DSKSSDKSVCLFTDFDSQTNVSQSKDSDVYITDKCVLDMRSMDFKSNSAVAWSNKSDFACANAF
NNSIIPEDTFFPSPESS m134

SEQ ID No: 10 Alpha chain (comprising SEQ ID NO: 7 and the constant domain of SEQ ID NO: 4,the last 8 amino acids at the C terminus are optional ). CDRs are underlined and mutations are shown in bold.

[A/Q] KEVEQNSGPLSVPEGAIASLNCTYSSWEGQSFFWYRQYSGKSPELIMFIYSNGDKED
GRFTAQLNKASQYISLLIRDSKLSDSATYLCAVRTNSGYALNFGKGTSLLVTPHIQKPDPAVYQLR
DSKSSDKSVCLFTDFDSQTNVSQSKDSDVYITDKCVLDMRSMDFKSNSAVAWSNKSDFACANAF
NNSIIPEDTFFPSPESS

Figure 6

Amino acid sequences beta chains of TCR-anti-CD3 fusions of the invention

SEQ ID No: 11 Beta chain (comprising an anti-CD3 scFv (grey) fused via a linker (italics) to a TCR beta chain comprising SEQ ID NO: 8 and the constant domain of SEQ ID NO: 5). CDRs are underlined and mutations are shown in bold.

AIQMTQSPSSLSASVGDRVTITCRASQDIRNYLNWYQQKPGKAPKLLIYYTSRLESGVPSRFSG

SGSGTDYTLTISSLQPEDFATYYCQQGNTLPWTFGQGTKVEIKGGGGSGGGGSGGGGSGGGGSG

GGSEVQLVESGGGLVQPGGSLRLSCAASGYSFTGYTMNWVRQAPGKGLEWVALINPYKGVSTYN

QKFKDRFTISVDKSKNTAYLQMNSLRAEDTAVYYCARSGYYGDSDWYFDVWGQGTLVTVSS*GGG*

*GS*DAGVTQSPTHLIKTRGQQVTLRCSPKSGHDTVSWYQQALGQGPQFIFQAVRGVERQRGNFPDRF

SGHQFPNYSSELNVNALLLGDSALYLCASSDTVSYEQYFGPGTRLTVTEDLKNVFPPEVAVFEPS

EAEISHTQKATLVCLATGFYPDHVELSWWVNGKEVHSGVCTDPQPLKEQPALNDSRYALSSRLR

VSATFWQDPRNHFRCQVQFYGLSENDEWTQDRAKPVTQIVSAEAWGRAD

TCR anti-CD3 fusion molecules demonstrate potent T cell redirection against cells presenting target peptide-HLA complex

A)

TCR anti-CD3 fusion molecules show no reactivity against antigen negative cells within a therapeutically relevant concentration TCR anti-CD3 fusion molecules demonstrate T cells redirection against target cells presenting low levels of peptide-HLA complex

ENGINEERED IMMUNE-MOBILIZING T-CELL RECEPTORS WITH ENHANCED AFFINITY FOR HIV-1 GAG

This application is a continuation of U.S. Application Ser. No. 16/087,041, filed Sep. 20, 2018, which is the National Stage of International Application No. PCT/GB2017/050805, filed Mar. 22, 2017, which claims the benefit of and priority to Great Britain Patent Application Serial No. 1604953.8, filed on Mar. 23, 2016, the contents of which are incorporated by reference in their entirety.

The instant application contains a Sequence Listing which has been submitted electronically via Patent Center in ST.26 XML format, and is hereby incorporated by reference in its entirety. Said XML copy, created on Nov. 29, 2022, is named 53150US_XML_sequencelisting, and is 44,071 bytes in size.

The present invention relates to T cell receptors (TCRs) which bind the HLA-A*02 restricted peptide SLYNTVATL (SEQ ID NO: 1) derived from the HIV Gag gene product, p17. Said TCRs comprise non-natural mutations within the alpha and/or beta variable domains relative to a native HIV TCR. The TCRs of the invention possess unexpectedly high affinity, specificity and sensitivity for a complex of SEQ ID NO: 1 and HLA-A*02, and drive a particularly potent T cell response. Such TCRs are particularly useful in the development of soluble immunotherapeutic reagents for the treatment of HIV infected individuals.

BACKGROUND TO THE INVENTION

The Human Immuno-deficiency Virus (HIV) is the causative agent of Acquired Immune Deficiency Syndrome (AIDS). The virus is an enveloped retrovirus belonging to the lentivirus group. Current treatments rely on the use of combination antiretroviral therapy (ART) to control viral infection. However, these treatments are unable to completely eradicate infection due to the stable integration of viral genes into host cell chromosomes, leading to the rapid establishment of a reservoir of long-lived, latently infected CD4+ T cells (Siliciano et al. 2003 Nat Med, 9, 727). Therefore, new treatments are required which have the potential to eradicate viral reservoirs and to achieve a functional cure. Immunotherapeutic strategies, and in particular those that result in the activation of CD8+ T cells, represent a promising approach (Vanham et al. 2012, Retrovirol 9, 72; Shan et al. 2012, Immunity 36, 491; Sloan et al. 2015, PLoS Pathog. 5; 11(11); Varela-Rohena et al. 2008, Nat Med, 14(12):1390-5). Such approaches may be combined with latency reversing agents.

Vaccines designed to stimulate the T cell response have been developed and used in combination with viral reactivation reagents; however, to date these have proved largely ineffective, possibly because the T cell clones activated are those that have failed to control the virus in the first place (Autran et al. 2008, AIDS 22, 1313; Schooley et al. 2012, J Infect Dis 202, 705; Casazza et al. 2013, J. Infect Dis 207, 1829). An alternative immunotherapeutic approach involves using engineered T cell receptors (TCRs) to generate a potent immune response against HIV infected cells. In nature, T cells and TCRs typically have a weak affinity for antigen, in the low micromolar to nanomolar range. Engineering the TCR by mutating the antigen recognition site can produce increases in antigen affinity which can lead to an enhanced immune response in vivo. In the context of HIV, the enhanced response should be sufficient to eradicate the virus from cells presenting low levels of antigen. Such engineered TCRs may be used in cellular therapy applications with gene modified T cells (see Vonderheide and June, 2014, Immunol Rev, 257, 7-13). Alternatively, engineered TCRs may be produced as soluble reagents for the purpose of delivering cytotoxic or immuno-stimulatory agents to the infected cells (Lissin, et al., (2013). "High-Affinity Monoclonal T-cell receptor (mTCR) Fusions. Fusion Protein Technologies for Biophamaceuticals: Applications and Challenges". S. R. Schmidt, Wiley; Boulter, et al., (2003), Protein Eng 16(9): 707-711; Liddy, et al., (2012), Nat Med 8: 980-987; WO03/020763). For soluble TCRs to be used as therapeutics it is desirable that the affinity $(K_D)$ and/or the binding half-life for antigen is particularly high, for example a $K_D$ in the picomolar range and/or a binding half-life of several hours. Such high affinities are required to drive a potent response against target cells presenting low levels of antigen. In all applications involving affinity engineered TCRs, it is essential that the TCRs not only have a higher affinity for antigen than the corresponding wild type TCR, but also retain a high level of antigen specificity. Loss of specificity in this context may result in off-target effects when such TCRs are administered to patients.

Affinity maturation typically involves the skilled person having to identify specific mutations and/or combinations of mutations, including but not limited to substitutions, insertions and/or deletions, that can be made to a WT TCR sequence in order to increase the strength of antigen recognition. Methods to identify mutations of a given TCR that confer an affinity enhancement are known in the art, for example the use of display libraries (Li et al., (2005) Nat Biotechnol. 23(3):349-354; Holler et al., (2000). Proc Natl Acad Sci USA; 97(10):5387-5392). However, to produce significant increases in the affinity of a given TCR against a given target requires the skilled person to select specific mutations and/or combinations of mutations from a large pool of possible alternatives. In many cases it may not be possible to achieve the desired affinity and specificity. The mutations required for high affinity and high specificity should also produce a TCR that is able to be expressed, refolded and purified at a reasonable yield and that is highly stable in a purified form.

The peptide sequence SLYNTVATL (SEQ ID NO 1) is derived from the p17 gene product of the Gag gene, one of nine genes which make up the HIV virus and to which T cell responses have been shown to be particularly effective in controlling viral load (Rolland et al. 2008, PLoS One, 3:e1424). The peptide (termed Gag herein) is presented by HLA-A*02 on the surface of HIV infected cells. Therefore, the Gag-HLA-A*02 complex provides an ideal target for the TCR-based recognition of HIV infected cells.

A WT TCR has been isolated that recognizes the Gag-HLA-A*02 complex, and various mutations within the WT TCR sequence have been identified that result in higher affinity recognition (WO06103429 and Varela-Rohena et al. 2008, Nat Med, 14(12):1390-5). CD8+ cytotoxic T cells transduced with said affinity enhanced TCRs were able to control HIV infection in vitro at suitable effector target ratios for T cell therapy. These TCRs were able to recognize all of the most common viral escape peptides (Varela-Rohena et al. 2008, Nat Med, 14(12):1390-5). While such TCRs have utility in adoptive T cell therapy, soluble TCRs for therapeutic use typically require higher affinity antigen recognition to be able to recognize infected cells presenting low epitope levels.

The inventors have unexpectedly found additional mutants of the same WT TCR that may be combined with one or more of the previously identified mutations to produce TCRs with particularly suitable properties for use in soluble TCR based therapeutics.

DETAILED DESCRIPTION OF THE INVENTION

In a first aspect, the present invention provides a T cell receptor (TCR) having the property of binding to SLYNT-VATL (SEQ ID No: 1) in complex with HLA-A*02 and comprising a TCR alpha chain variable domain and a TCR beta chain variable domain, the alpha chain variable domain comprising an amino acid sequence that has at least 90% identity to the sequence of amino acid residues 1-112 of SEQ ID No: 2, and/or the beta chain variable domain comprising an amino acid sequence that has at least 90% identity to the sequence of amino acid residues 1-113 of SEQ ID No: 3, wherein the alpha chain variable domain has at least one of the following mutations

TABLE 1

| | |
|---|---|
| D28 | S |
| R29 | W |
| G30 | E |
| S31 | G |
| I51 | L |
| S53 | A |
| N54 | D |
| G55 | P | with reference to the numbering shown in SEQ ID No: 2, and/or the beta chain variable domain has at least one of the following mutations:

TABLE 2

| | |
|---|---|
| Y50 | A | optionally in combination with at least one of the following mutations:

TABLE 3

| | |
|---|---|
| Y51 | V |
| E52 | R |
| E53 | G |
| E54 | V | with reference to the numbering shown in SEQ ID No: 3.

The present invention discloses TCRs that possess unexpectedly good antigen binding properties, including picomolar antigen affinity, a long binding half-life, and the ability to mediate potent immune activation, when fused to an activating moiety, against HIV infected cells presenting extremely low levels of antigen, whilst maintaining a high level of specificity. The TCRs of the invention are particularly suitable for use as soluble targeting reagents in treating HIV infected individuals. In particular, TCRs in accordance with the invention unexpectedly have a high antigen affinity relative to the wild-type Gag TCR and high antigen specificity. The perception in the art is that engineering TCRs to possess high affinity for antigen will also result in TCRs with reduced antigen specificity. For example, dramatic increases in affinity have been associated with a loss of antigen specificity in TCR gene-modified CD8 T cells, which could result in the nonspecific activation of these TCR-transfected CD8 cells (see Zhao et al., (2007) *J Immunol.* 179: 5845-54;

Robbins et al., (2008) *J Immunol.* 180: 6116-31; and WO2008/038002). Furthermore, it has been shown that soluble high affinity TCRs fused to anti-CD3 can lose specificity for antigen when used at high concentrations (see Liddy et al., (2012), *Nat Med,* 8: 180-187). Specificity concerns are a particular consideration for high affinity TCRs derived from this WT Gag TCR since the WT TCR has a broad epitope recognition profile, capable of tolerating single alanine substitutions at any side chain position of the Gag peptide and even recognizing a multiple alanine substituted peptide (Varela-Rohena et al. 2008, Nat Med, 14(12) 1390-5 and references therein). Contrary to the perception in the art, the inventors have found mutant TCRs that have both high affinity and high specificity, and are therefore particularly suitable for clinical applications.

The TCR sequences defined herein are described with reference to IMGT nomenclature which is widely known and accessible to those working in the TCR field. For example, see: LeFranc and LeFranc, (2001). "T cell Receptor Factsbook", Academic Press; Lefranc, (2011), Cold Spring Harb Protoc 2011(6): 595-603; Lefranc, (2001), Curr Protoc Immunol Appendix 1: Appendix 1O; and Lefranc, (2003), Leukemia 17(1): 260-266. Briefly, αγ TCRs consist of two disulphide linked chains. Each chain (alpha and beta) is generally regarded as having two domains, namely a variable and a constant domain. A short joining region connects the variable and constant domains and is typically considered part of the alpha variable region. Additionally, the beta chain usually contains a short diversity region next to the joining region, which is also typically considered part of the beta variable region.

The variable domain of each chain is located N-terminally and comprises three Complementarity Determining Regions (CDRs) embedded in a framework sequence. The CDRs comprise the recognition site for peptide-MHC binding. There are several genes coding for alpha chain variable (Vα) regions and several genes coding for beta chain variable (Vβ) regions, which are distinguished by their framework, CDR1 and CDR2 sequences, and by a partly defined CDR3 sequence. The Vα and Vβ genes are referred to in IMGT nomenclature by the prefix TRAV and TRBV respectively (Folch and Lefranc, (2000), Exp Clin Immunogenet 17(1): 42-54; Scaviner and Lefranc, (2000), Exp Clin Immunogenet 17(2): 83-96; LeFranc and LeFranc, (2001), "T cell Receptor Factsbook", Academic Press). Likewise there are several joining or J genes, termed TRAJ or TRBJ, for the alpha and beta chain respectively, and for the beta chain, a diversity or D gene termed TRBD (Folch and Lefranc, (2000), Exp Clin Immunogenet 17(2): 107-114; Scaviner and Lefranc, (2000), Exp Clin Immunogenet 17(2): 97-106; LeFranc and LeFranc, (2001), "T cell Receptor Factsbook", Academic Press). The huge diversity of T cell receptor chains results from combinatorial rearrangements between the various V, J and D genes, which include allelic variants, and junctional diversity (Arstila, et al., (1999), Science 286(5441): 958-961; Robins et al., (2009), Blood 114(19): 4099-4107.) The constant, or C, regions of TCR alpha and beta chains are referred to as TRAC and TRBC respectively (Lefranc, (2001), Curr Protoc Immunol Appendix 1: Appendix 1O).

The term 'native TCR' is used synonymously in this application with the terms 'wild type TCR' or 'WT TCR' or 'non-mutated TCR' to mean a TCR having an alpha chain variable domain comprising TRAV12-2*01 with the following mutations relative to a canonical TRAV12-2 sequence: V731, Q81 K and P82L based on the numbering of SEQ ID NO 2 and the CDR3 amino acid sequence AVRTNSGYALN (SEQ ID NO: 22), and a beta chain variable domain comprising TRBV5-6*01 and the CDR3 amino acid sequence ASSDTVSYEQY (SEQ ID NO: 25). Amino acid sequences of the native alpha and beta variable domains are provided by residues 1-112 of SEQ ID NO: 2 and residues 1-113 of SEQ ID NO: 3, as shown in FIG. 1 [note that in comparison to the previous published sequences (see WO06103429 and Varela-Rohena et al. 2008, Nat Med, 14(12):1390-5), the residue following the initiation methionine of TRBV is denoted as aspartic acid (D) rather than glutamic acid (E). Aspartic acid is the canonical residue at this position for TRBV5-6*01 and was re-introduced during engineering. For a similar reason the residue following the initiation methionine of TRAV is Q rather than A as noted in the previously published sequence]. In TCRs of the present certain preferred embodiments the alpha chain variable domain has at least one of the following groups of mutations:

Group 1: D27S, R28W, G29E, S30G

Group 2: I50L, S52A, N53D, G54P

Group 3: D27S, R28W, G29E, S30G, I50L, S52A, N53D, G54P and/or the beta chain variable domain has the following group of mutations:

Group 1: Y49A, E50V, E51R, E52G, E53V

In certain preferred embodiments the sequence of CDR1, CDR2 and CDR3 of the alpha and/or beta chain may be selected from the following tables, with reference to the numbering of SEQ ID NOs: 2 and 3 respectively.

TABLE 4

| Alpha chain CDRs | | |
|---|---|---|
| CDR1 (28-33) | CDR2 (51-56) | CDR3 (91-101) |
| SWEGQS (SEQ ID NO: 26) | LYADPD (SEQ ID NO: 27) | AVRTNSGYALN (SEQ ID NO: 22) |
| SWEGQS (SEQ ID NO: 26) | IYSNGD (SEQ ID NO: 21) | AVRTNSGYALN (SEQ ID NO: 22) |

TABLE 5

| Beta chain CDRs | | |
|---|---|---|
| CDR1 (28-32) | CDR2 (50-55) | CDR3 (93-103) |
| SGHDT (SEQ ID NO: 23) | AVRGVE (SEQ ID NO: 28) | ASSDTVSYEQY (SEQ ID NO: 25) | invention, the initiation methionine residue at the N terminus of the respective alpha and beta chain variable domains is optional. In addition or alternatively, the residue following the initiation methionine of the alpha chain variable domain may be alanine (A) or glutamine (Q).

The constant domain of the WT TCR may be full length, or may be truncated and/or mutated to produce a soluble TCR. In either case cysteine substitutions may be introduced into the TRAC and TRBC regions such that a non-native interchain disulphide bond can be formed. Suitable positions for the location of said cysteine substitutions are described in WO03020763. FIG. 2 shows the extracellular sequences of the wild type TCR alpha and beta chains respectively, in soluble format. SEQ ID NO: 4 is identical to the native alpha chain extracellular sequence SEQ ID NO: 2 except that the cysteine at position 48 of the constant domain has been replaced with threonine. The alpha chain constant domain may be truncated by 8 amino acids at its C terminus (FFPSPESS). Likewise SEQ ID NO: 5 is identical to the native beta chain extracellular sequence SEQ ID NO: 3 except that cysteine at position 57 of the constant domain has been replaced with serine, cysteine at position 75 of the constant domain has been replaced with alanine, and asparagine at position 89 of the constant domain has been replaced with aspartic acid. The soluble wild-type TCR may be used to provide a reference against which the binding profile of the mutated TCRs of the invention may be compared. Such sequences are particularly suitable for use as therapeutic TCRs for targeted immunotherapy of cancers that present SLYNTVATL HLA-A*02 complex.

In certain embodiments the alpha chain variable domain of the TCR of the present invention may have between 4 and 8 mutations and/or the beta chain may have 5 mutations. In The invention also provides a TCR that binds to SLYNTVATL (SEQ ID No: 1) in complex with HLA-A*02, wherein: the alpha chain CDRs 1, 2 and 3 comprise SEQ ID NOs: 26, 27 and 22 respectively or SEQ ID NOs: 26, 21 and 22 respectively, and/or the beta chain CDRs 1, 2 and 3 comprise SEQ ID NOs: 23, 28 and 25 respectively; and/or at least one of the CDRs contains one or more conservative substitutions with respect to SEQ ID NOs: 21-23 and 25-28; and/or at least one of the CDRs contains up to three tolerated substitutions with respect to SEQ ID NOs: 21-23 and 25-28. Preferably said substitutions do not change the binding affinity and/or a binding half-life (T½) by more than +/−50%, or more preferably by no more than +/−20%, relative the non-substituted TCR.

In some embodiments, the α chain variable domain of the TCR of the invention may comprise an amino acid sequence that has at least 90%, at least 91%, at least 92%, at least 93%, at least 94%, at least 95%, at least 96%, at least 97%, at least 98% or at least 99% identity to the sequence of amino acid residues 1-112 or 2-112 (as the initiation methionine residue at the N terminus is optional) of SEQ ID NO: 2, provided that the α chain variable domain has at least one of the mutations or groups of mutations of the invention outlined above. In addition, the residue following the initiation methionine of the alpha chain variable domain may be alanine (A) rather than glutamine (Q). In some embodiments, the β chain variable domain of the TCR of the invention may comprise an amino acid sequence that has at least 90%, at least 91%, at least 92%, at least 93%, at least 94%, at least 95%, at least 96%, at least 97%, at least 98% or at least 99% identity to the sequence of amino acid residues 1-113 or 2-113 (as the initiation methionine residue at the N terminus is optional) of SEQ ID NO: 3, provided that the β chain variable domain has at least one of the mutations or groups of mutations of the invention outlined above.

The amino acid sequence of the CDR3 of the alpha chain variable domain may be identical to the sequence of the CDR3 of the alpha chain of the wild type TCR. Additionally or alternatively, the amino acid sequence of the CDR3 of the beta chain variable domain may be identical to the sequence of the CDR3 of the beta chain of the wild type TCR.

In certain preferred TCRs of the invention the alpha chain variable domain may comprise the amino acid sequence of SEQ ID NO: 6 or 7, and/or the beta chain variable domain may comprise the amino acid sequence of SEQ ID NO: 8. As noted, in TCRs of the present invention, the initiation methionine residue at the N terminus of the respective alpha and beta chain variable domains is optional. In addition or alternatively, the residue following the initiation methionine of the alpha chain variable domain (position 1 in SEQ ID NO: 6 and 7) may be alanine (A) or glutamine (Q).

Within the scope of the invention are phenotypically silent variants of any TCR of the invention disclosed herein. As used herein the term "phenotypically silent variants" is understood to refer to a TCR which incorporates one or more further amino acid changes, including substitutions, insertions and deletions, in addition to those set out above, which TCR has a similar phenotype to the corresponding TCR without said change(s). For the purposes of this application, TCR phenotype comprises antigen binding affinity ($K_D$ and/or binding half-life) and antigen specificity. A phenotypically silent variant may have a $K_D$ and/or binding half-life for the SLYNTVATL (SEQ ID NO: 1) HLA-A*02 complex within 50%, or more preferably within 20%, of the measured $K_D$ and/or binding half-life of the corresponding TCR without said change(s), when measured under identical conditions (for example at 25° C. and on the same SPR chip). Suitable conditions are further provided in Example 3. Antigen specificity is further defined below. As is known to those skilled in the art, it may be possible to produce TCRs that incorporate changes in the variable domains thereof compared to those detailed above without altering the affinity of the interaction with the SLYNTVATL (SEQ ID NO: 1) HLA-A*02 complex. In particular, such silent mutations may be incorporated within parts of the sequence that are known not to be directly involved in antigen binding (e.g. the framework regions, or parts of the CDRs that do not contact the peptide antigen). Such trivial variants are included in the scope of this invention. As is known in the art, further amino acid changes may be incorporated for reasons such as improving stability and/or manufacturability. Additional or alternatively further amino acid changes may be made to reduce the potential for immunogenicity in vivo. Such mutations are included within the scope of the invention provided that they are phenotypically silent Phenotypically silent variants may be produced by incorporating one or more conservative substitutions and/or one or more tolerated substitutions. By tolerated substitutions it is meant those substitutions which do not fall under the definition of conservative as provided below but are nonetheless phenotypically silent. By conservative substitutions it is meant the substitutions of one or more amino acids with alternative amino acids having sharing similar properties. The skilled person is aware that various amino acids have similar properties and thus are 'conservative'. One or more such amino acids of a protein, polypeptide or peptide can often be substituted by one or more other such amino acids without eliminating a desired activity of that protein, polypeptide or peptide. Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains). It should be appreciated that amino acid substitutions within the scope of the present invention can be made using naturally occurring or non-naturally occurring amino acids. For example, it is contemplated herein that the methyl group on an alanine may be replaced with an ethyl group, and/or that minor changes may be made to the peptide backbone. Whether or not natural or synthetic amino acids are used, it is preferred that only L-amino acids are present.

The present invention therefore extends to use of TCR comprising an amino acid sequence having at least 90% identity, such as 90%, 91%, 92%, 93%, 94%, 95%, 96%, 97%, 98%, 99% or 100% identity, to a TCR wherein the alpha variable domain comprises the amino acid sequence of SEQ ID NOs: 6 and 7, and/or the beta variable domain comprises the amino acid sequence of SEQ ID NO: 8.

"Identity" as known in the art is the relationship between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. While there exist a number of methods to measure identity between two polypeptide or two polynucleotide sequences, methods commonly employed to determine identity are codified in computer programs. Preferred computer programs to determine identity between two sequences include, but are not limited to, GCG program package (Devereux, et al., Nucleic Acids Research, 12, 387 (1984), BLASTP, BLASTN, and FASTA (Atschul et al., J. Molec. Biol. 215, 403 (1990)).

One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of identity analysis are contemplated in the present invention.

The percent identity of two amino acid sequences or of two nucleic acid sequences is determined by aligning the sequences for optimal comparison purposes (e.g., gaps can be introduced in the first sequence for best alignment with the sequence) and comparing the amino acid residues or nucleotides at corresponding positions. The "best alignment" is an alignment of two sequences which results in the highest percent identity. The percent identity is determined by the number of identical amino acid residues or nucleotides in the sequences being compared (i.e., % identity=number of identical positions/total number of positions×100).

The determination of percent identity between two sequences can be accomplished using a mathematical algorithm known to those of skill in the art. An example of a mathematical algorithm for comparing two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. The NBLAST and XBLAST programs of Altschul, et al. (1990) J. Mol. Biol. 215:403-410 have incorporated such an algorithm. BLAST nucleotide searches can be performed with the NBLAST program, score=100, wordlength=12 to obtain nucleotide sequences homologous to nucleic acid molecules. BLAST protein searches can be performed with the XBLAST program, score=50, wordlength=3 to obtain amino acid sequences homologous to protein molecules for use in the invention. To obtain gapped alignments for comparison purposes, Gapped BLAST can be utilised as described in Altschul et al. (1997) Nucleic Acids Res. 25:3389-3402. Alternatively, PSI-Blast can be used to perform an iterated search which detects distant relationships between molecules (Id.). When utilising BLAST, Gapped BLAST, and PSI-Blast programs, the default parameters of the respective programs (e.g., XBLAST and NBLAST) can be used. See http://www.ncbi.nlm.nih.gov. Another example of a mathematical algorithm utilised for the comparison of sequences is the algorithm of Myers and Miller, CABIOS (1989). The ALIGN program (version 2.0) which is part of the CGC sequence alignment software package has incorporated such an algorithm. Other algorithms for sequence analysis known in the art include ADVANCE and ADAM as described in Torellis and Robotti (1994) Comput. Appl. Biosci., 10: 3-5; and FASTA described in Pearson and Lipman (1988) Proc. Natl. Acad. Sci. 85:2444-8. Within FASTA, ktup is a control option that sets the sensitivity and speed of the search.

Mutations, including conservative and tolerated substitutions, insertions and deletions, may be introduced into the sequences provided using any appropriate method including, but not limited to, those based on polymerase chain reaction (PCR), restriction enzyme-based cloning, or ligation independent cloning (LIC) procedures. These methods are detailed in many of the standard molecular biology texts. For further details regarding polymerase chain reaction (PCR) and restriction enzyme-based cloning, see Sambrook & Russell, (2001) Molecular Cloning—A Laboratory Manual (3$^{rd}$ Ed.) CSHL Press. Further information on ligation independent cloning (LIC) procedures can be found in Rashtchian, (1995) Curr Opin Biotechnol 6(1): 30-6. The TCR sequences provided by the invention may be obtained from solid state synthesis, or any other appropriate method known in the art.

The TCRs of the invention have the property of binding the SLYNTVATL (SEQ ID No: 1) HLA-A*02 complex. TCRs of the invention have been found to be highly specific for this epitope relative to other, irrelevant epitopes, and are thus particularly suitable as targeting vectors for delivery of therapeutic agents or detectable labels to cells and tissues displaying those epitopes. Specificity in the context of TCRs of the invention relates to their ability to recognise HLA-A*02 target cells that are antigen positive, whilst having minimal ability to recognise HLA-A*02 target cells that are antigen negative.

Specificity can be measured in vitro, for example, in cellular assays such as those described in Example 5. To test specificity the TCRs may be in soluble form and/or may be expressed on the surface of T cells. Recognition may be determined by measuring the level of T cell activation in the presence of a TCR of the invention and target cells. Minimal recognition of antigen negative target cells is defined as a level of T cell activation of less than 20%, preferably less than 10%, preferably less than 5%, and more preferably less than 1%, of the level produced in the presence of antigen positive target cells, when measured under the same conditions and at a therapeutically relevant TCR concentration. For soluble TCRs of the invention a therapeutically relevant concentration may be defined as a TCR concentration of $10^{-9}$ M or below, and/or a concentration of up to 100, preferably up to 1000, fold greater than the corresponding $EC_{50}$ value. Antigen positive cells may be obtained by peptide-pulsing using a suitable peptide concentration to obtain a low level of antigen presentation (for example, $10^{-9}$ M peptide, as described in Bossi et al., (2013) Oncoimmunol. 1;2 (11):e26840) or, they may naturally present said peptide. Preferably, antigen negative cells are human cells.

Specificity may additionally, or alternatively, relate to the ability of a TCR to bind to SLYNTVATL (SEQ ID NO: 1) HLA-A*02 complex and not to a panel of alternative peptide-HLA complexes. Preferably, the alternative peptide-HLA complexes comprise HLA-A*02. This may, for example, be determined by the Biacore method of Example 3. The alternative peptides may share a low level of sequence identity with SEQ ID NO: 1 and may be naturally presented. Preferably, the alternative peptides are presented on the surface of cells derived from normal human tissues, (i.e. cells not infected with HIV). Binding to SLYNTVATL-HLA-A*02 complex may be at least 2 fold greater than to other naturally-presented peptide HLA complexes, more preferably at least 10 fold, or at least 50 fold or at least 100 fold greater, even more preferably at least 400 fold greater.

An alternative or additional approach to determine TCR specificity may be to identify the peptide recognition motif of the TCR using sequential mutagenesis, e.g. alanine scanning. Such an approach is further described in Cameron et al., (2013), Sci Transl Med. 2013 Aug. 7; 5 (197): 197ra103 and WO2014096803.

TCRs of the invention may additionally bind to complexes containing natural escape variants of SEQ ID NO: 1 presented by HLA-A*02. Escape variants of the peptide SLYNTVATL have been isolated from AIDS patients and include the following (Sewell et al., (1997) Eur J Immunol. 27: 2323-2329):

|  |  |
|---|---|
| SLFNTVATL | (SEQ ID NO: 20) |
| SLFNTVAVL | (SEQ ID NO: 21) |
| SLSNTVATL | (SEQ ID NO: 22) |
| SSFNTVATL | (SEQ ID NO: 23) |
| SLLNTVATL | (SEQ ID NO: 24) |
| SLYNTIATL | (SEQ ID NO: 25) |
| SLYNTIAVL | (SEQ ID NO: 26) |

-continued

```
                                   (SEQ ID NO: 27)
SLFNTIATL (SEQ ID NO: 28)
SLFNTIAVL (SEQ ID NO: 29)
SLFNFVATL
```

Certain TCRs of the invention may have an ideal safety profile for use as therapeutic reagents. In this case the TCRs may be in soluble form and may preferably be fused to an immune effector. An ideal safety profile means that in addition to demonstrating good specificity, the TCRs of the invention may have passed further preclinical safety tests. Examples of such tests include whole blood assays to confirm minimal cytokine release in the presence of whole blood and thus low risk of causing a potential cytokine release syndrome in vivo, and alloreactivity tests to confirm low potential for recognition of alternative HLA types.

Certain soluble TCRs of the invention may be amenable to high yield purification. High yield means greater than 1%, or more preferably greater than 10%, or higher yield.

TCRs of the invention may have a $K_D$ for the complex of less than 100 nM, for example from about 50 nM to about 1 pM and/or have a binding half-life (T½) for the complex in the range of from about 1 min to about 50 h or more. Certain TCRs of the invention may have a $K_D$ for the complex of from about 1 pM to about 1 nM, from about 1 pM to about 500 pM, from about 1 pM to about 300 pM. Certain TCRs of the invention may have a $K_D$ for the complex of about 50 pM to about 200 pM. TCRs of the invention may have a binding half-life (T½) for the complex in the range of from about 1 min to about 50 h or more (such as 100 h), from about 30 min to about 50 h or more (such as 100 h), or from about 6 h to about 50 h or more (such as 100 h). All such TCRs are highly suitable for use as therapeutics and/or diagnostics when coupled to a detectable label or therapeutic agent. Certain TCRs of the invention may be suitable for adoptive therapy applications, such TCRs may have a $K_D$ for the complex of from about 50 nM to about 100 nM, and/or a binding half-life for the complex of from about 30s sec to about 12 min.

Certain preferred TCRs are able to generate a highly potent T cell response in vitro against antigen positive cells, in particular those cells presenting low levels of antigen typical of HIV infected CD4 cells. Such TCRs may be in soluble form and linked to an immune effector such as an anti-CD3 antibody. The T cell response that is measured may be the release of T cell activation markers such as Interferon γ or Granzyme B, or cell killing, or other measure of T cell activation as known to those skilled in the art. Preferably a highly potent response is one with $EC_{50}$ value in the pM range, for example 100 pM or lower, preferable 50 pM or lower, for example between 50 pM and 1 pM.

Certain preferred TCRs of the invention have a binding affinity for, and/or a binding half-life for, the SLYNTVATL-HLA-A*02 complex substantially higher than that of the native TCR. Increasing the binding affinity of a native TCR often reduces the specificity of the TCR for its peptide-MHC ligand, and this is demonstrated in Zhao et al., (2007) J. Immunol, 179:9, 5845-5854. However, such TCRs of the invention remain specific for the SLYNTVATL-HLA-A*02 complex, despite having substantially higher binding affinity than the native TCR.

Binding affinity (inversely proportional to the equilibrium constant $K_D$) and binding half-life (expressed as T½) can be determined using the Surface Plasmon Resonance (BIA-core) and/or the Octet method of Example 3 herein. It will be appreciated that doubling the affinity of a TCR results in halving the $K_D$. T½ is calculated as In2 divided by the off-rate ($k_{off}$). Therefore, doubling of T½ results in a halving in $k_{off}$. $K_D$ and $k_{off}$ values for TCRs are usually measured for soluble forms of the TCR, i.e. those forms which are truncated to remove cytoplasmic and transmembrane domain residues. Preferably the binding affinity or binding half-life of a given TCR is measured several times, for example 3 or more times, using the same assay protocol and an average of the results is taken.

For use as a targeting agent for delivering therapeutic agents to the antigen presenting cell the TCR may be in soluble form (i.e. having no transmembrane or cytoplasmic domains). For stability, TCRs of the invention, and prefer-ably soluble αβ heterodimeric TCRs, may have an intro-duced disulphide bond between residues of the respective constant domains, as described, for example, in WO 03/020763. One or both of the extracellular constant domains present in an αβ heterodimer of the invention may be truncated at the C terminus or C termini, for example by up to 15, or up to 10 or up to 8 or fewer amino acids. For use in adoptive therapy, an αβ heterodimeric TCR may, for example, be transfected as full length chains having both cytoplasmic and transmembrane domains. TCRs for use in adoptive therapy may contain a disulphide bond correspond-ing to that found in nature between the respective alpha and beta constant domains, additionally or alternatively a non-native disulphide bond may be present.

The TCRs of the invention may be αβ heterodimers. TCRs of the invention may be in single chain format. Single chain formats include, but are not limited to, αβ TCR polypeptides of the Vα-L-Vβ, Vβ-L-Vα, Vα-Cα-L-Vβ, Vα-L-Vβ-Cβ, Vα-Cα-L-Vβ-Cβ or Vβ-Cβ-L-Vα-Cα types, wherein Vα and Vβ are TCR α and β variable regions respectively, Cα and Cβ are TCR α and β constant regions respectively, and L is a linker sequence (Weidanz et al., (1998) J Immunol Methods. 1; 221(1-2):59-76; Epel et al., (2002), Cancer Immunol Immunother. 51(10):565-73; WO 2004/033685; WO9918129). One or both of the constant domains may be full length, or they may be truncated, and/or contain mutations. In certain embodiments single chain TCRs of the invention may have an introduced disulphide bond between residues of the respective constant domains, as described in WO 2004/033685. Single chain TCRs are further described in WO2004/033685; WO98/39482; WO01/62908; Weidanz et al. (1998) J Immunol Methods 221(1-2): 59-76; Hoo et al. (1992) Proc Natl Acad Sci USA 89(10): 4759-4763; Schodin (1996) Mol Immunol 33(9): 819-829).

As will be obvious to those skilled in the art, it may be possible to truncate the sequences provided at the C-termi-nus and/or N-terminus thereof, by 1, 2, 3, 4, 5 or more residues, without substantially affecting the binding charac-teristics of the TCR. All such trivial variants are encom-passed by the present invention.

Alpha-beta heterodimeric TCRs of the invention usually comprise an alpha chain TRAC constant domain sequence and/or a beta chain TRBC1 or TRBC2 constant domain sequence. The alpha and beta chain constant domain sequences may be modified by truncation or substitution to delete the native disulphide bond between Cys4 of exon 2 of TRAC and Cys2 of exon 2 of TRBC1 or TRBC2. The alpha and/or beta chain constant domain sequence(s) may also be modified by substitution of cysteine residues for Thr 48 of TRAC and Ser 57 of TRBC1 or TRBC2, the said cysteines forming a disulphide bond between the alpha and beta constant domains of the TCR. TRBC1 or TRBC2 may additionally include a cysteine to alanine mutation at position 75 of the constant domain and an asparagine to aspartic acid mutation at position 89 of the constant domain.

The constant domain may additionally or alternatively contain further mutations, substitutions or deletions relative to the native TRAC and/or TRBC1/2 sequences. The term TRAC and TRBC1/2 encompasses natural polymophic variants, for example N to K at position 4 of TRAC (Bragado et al *Int Immunol,* 1994 February; 6(2):223-30).

Also included with the scope of the invention are variants, fragments and derivatives of the TCRs provided by the invention.

The invention also includes particles displaying TCRs of the invention and the inclusion of said particles within a library of particles. Such particles include but are not limited to phage, yeast ribosomes, or mammalian cells. Method of producing such particles and libraries are known in the art (for example see WO2004/044004; WO01/48145, Chervin et al. (2008) J. Immuno. Methods 339.2: 175-184).

In a further aspect, the present invention provides nucleic acid encoding a TCR of the invention and/or TCR-anti-CD3 fusion molecule of the invention. In some embodiments, the nucleic acid is cDNA. In some embodiments, the invention provides nucleic acid comprising a sequence encoding an α chain variable domain of a TCR of the invention. In some embodiments, the invention provides nucleic acid comprising a sequence encoding a β chain variable domain of a TCR of the invention. The nucleic acid may be non-naturally occurring and/or purified and/or engineered. For example, the nucleic acid may be codon optimised for a particular expression systems.

In another aspect, the invention provides a vector which comprises nucleic acid of the invention. Preferably the vector is a TCR expression vector.

The invention also provides a cell harbouring a vector of the invention, preferably a TCR expression vector. The vector may comprise nucleic acid of the invention encoding in a single open reading frame, or two distinct open reading frames, the alpha chain and the beta chain respectively. Another aspect provides a cell harbouring a first expression vector which comprises nucleic acid encoding the alpha chain of a TCR of the invention, and a second expression vector which comprises nucleic acid encoding the beta chain of a TCR of the invention. Such cells are particularly useful in adoptive therapy. The cells of the invention may be isolated and/or recombinant and/or non-naturally occurring and/or engineered.

Since the TCRs of the invention have utility in adoptive therapy, the invention includes a non-naturally occurring and/or purified and/or or engineered cell, especially a T-cell, presenting a TCR of the invention. The invention also provides an expanded population of T cells presenting a TCR of the invention. There are a number of methods suitable for the transfection of T cells with nucleic acid (such as DNA, cDNA or RNA) encoding the TCRs of the invention (see for example Robbins et al., (2008) *J Immunol.* 180: 6116-6131). T cells expressing the TCRs of the invention will be suitable for use in adoptive therapy-based treatment of HIV infection. As will be known to those skilled in the art, there are a number of suitable methods by which adoptive therapy can be carried out (see for example Rosenberg et al., (2008) *Nat Rev Cancer* 8(4): 299-308).

Soluble TCRs of the invention are useful for delivering detectable labels or therapeutic agents to antigen presenting cells and tissues containing antigen presenting cells. They may therefore be associated (covalently or otherwise) with a detectable label (for diagnostic purposes wherein the TCR is used to detect the presence of cells presenting the SLYN-TVATL-HLA-A2 complex); a therapeutic agent; or a PK modifying moiety.

Examples of PK modifying moieties include, but are not limited to, PEG (Dozier et al., (2015) Int J Mol Sci. October 28; 16(10):25831-64 and Jevsevar et al., (2010) Biotechnol J. January; 5(1):113-28), PAS (Schlapschy et al., (2013) Protein Eng Des Sel. August; 26(8):489-501), albumin (Dennis et al., (2002) J Biol Chem. September 20; 277(38): 35035-43) and/or unstructured polypeptides (Schellenberger et al., (2009) Nat Biotechnol. December; 27(12):1186-90).

Detectable labels for diagnostic purposes include for instance, fluorescent labels, radiolabels, enzymes, nucleic acid probes and contrast reagents.

Therapeutic agents which may be associated with the TCRs of the invention include immunomodulators, radio-active compounds, enzymes (perforin for example) or che-motherapeutic agents (cis-platin for example). To ensure that toxic effects are exercised in the desired location the toxin could be inside a liposome linked to TCR so that the compound is released slowly. This will prevent damaging effects during the transport in the body and ensure that the toxin has maximum effect after binding of the TCR to the relevant antigen presenting cells.

Other suitable therapeutic agents include:

small molecule cytotoxic agents, i.e. compounds with the ability to kill mammalian cells having a molecular weight of less than 700 Daltons. Such compounds could also contain toxic metals capable of having a cytotoxic effect. Furthermore, it is to be understood that these small molecule cytotoxic agents also include pro-drugs, i.e. compounds that decay or are converted under physiological conditions to release cytotoxic agents. Examples of such agents include cis-platin, maytansine derivatives, rachelmycin, calicheamicin, docetaxel, etoposide, gemcitabine, ifosfamide, irinote-can, melphalan, mitoxantrone, sorfimer sodiumphotof-rin II, temozolomide, topotecan, trimetreate glucuro-nate, auristatin E vincristine and doxorubicin;

peptide cytotoxins, i.e. proteins or fragments thereof with the ability to kill mammalian cells. For example, ricin, diphtheria toxin, pseudomonas bacterial exotoxin A, DNase and RNase;

radio-nuclides, i.e. unstable isotopes of elements which decay with the concurrent emission of one or more of α or β particles, or γ rays. For example, iodine 131, rhenium 186, indium 111, yttrium 90, bismuth 210 and 213, actinium 225 and astatine 213; chelating agents may be used to facilitate the association of these radio-nuclides to the high affinity TCRs, or multimers thereof;

immuno-stimulants, i.e. immune effector molecules which stimulate immune response. For example, cyto-kines such as IL-2 and IFN-γ, Superantigens and mutants thereof;

TCR-HLA fusions, e.g. fusion to a peptide-HLA complex, wherein said peptide is derived from a common human pathogen, such as Epstein Barr Virus (EBV);

chemokines such as IL-8, platelet factor 4, melanoma growth stimulatory protein, etc;

antibodies or fragments thereof, including anti-T cell or NK cell determinant antibodies (e.g. anti-CD3, anti-CD28 or anti-CD16);

alternative protein scaffolds with antibody like binding characteristics complement activators;

xenogeneic protein domains, allogeneic protein domains, viral/bacterial protein domains, viral/bacterial peptides.

One preferred embodiment is provided by a TCR of the invention associated (usually by fusion to an N- or C-terminus of the alpha or beta chain) with an anti-CD3 antibody, or a functional fragment or variant of said anti-CD3 antibody. As used herein, the term "antibody" encompasses such fragments and variants, including humanised variants. Examples of anti-CD3 antibodies include but are not limited to OKT3, UCHT-1, BMA-031 and 12F6. Antibody fragments and variants/analogues which are suitable for use in the compositions and methods described herein include minibodies, Fab fragments, F(ab')$_2$ fragments, dsFv and scFv fragments, Nanobodies™ (these constructs, marketed by Ablynx (Belgium), comprise synthetic single immunoglobulin variable heavy domain derived from a camelid (e.g. camel or llama) antibody) and Domain Antibodies (Domantis (Belgium), comprising an affinity matured single immunoglobulin variable heavy domain or immunoglobulin variable light domain) or alternative protein scaffolds that exhibit antibody like binding characteristics such as Affibodies (Affibody (Sweden), comprising engineered protein A scaffold) or Anticalins (Pieris (Germany)), comprising engineered anticalins) to name but a few.

Linkage of the TCR and the anti-CD3 antibody may be direct, or indirect via a linker sequence. Linker sequences are usually flexible, in that they are made up primarily of amino acids such as glycine, alanine and serine which do not have bulky side chains likely to restrict flexibility. Usable or optimum lengths of linker sequences are easily determined. Often the linker sequence will be less than about 12, such as less than 10, or from 2-10 amino acids in length. Suitable linkers that may be used in TCRs of the invention include, but are not limited to: GGGGS (SEQ ID No: 12), GGGSG (SEQ ID No: 13), GGSGG (SEQ ID No: 14), GSGGG (SEQ ID No: 15), GSGGGP (SEQ ID No: 16), GGEPS (SEQ ID No: 17), GGEGGGP (SEQ ID No: 18), and GGEGGGSEGGGS (SEQ ID No: 19) (as described in WO2010/133828).

Specific embodiments of anti-CD3-TCR fusion constructs of the invention include those which have an alpha chain variable domain selected from SEQ ID No: 6, or SEQ ID No: 7, and the TCR beta chain is SEQ ID No: 8 fused to an amino acid sequence corresponding to anti-CD3. Said alpha and beta chains may further comprise a truncated constant region having a non-native disulphide bond. The N or C terminus of the alpha and or beta chain may be fused to an anti-CD3 scFv antibody fragment via a linker selected from SEQ ID NOs: 12-19. Certain preferred embodiments of such anti-CD3-TCR fusion constructs are provided below:

TABLE 6

| Alpha chain SEQ ID NO | Beta Chain SEQ ID NO |
|---|---|
| 9 | 11 |
| 10 | 11 |

For some purposes, the TCRs of the invention may be aggregated into a complex comprising several TCRs to form a multivalent TCR complex. There are a number of human proteins that contain a multimerisation domain that may be used in the production of multivalent TCR complexes. For example the tetramerisation domain of p53 which has been utilised to produce tetramers of scFv antibody fragments which exhibited increased serum persistence and significantly reduced off-rate compared to the monomeric scFv fragment (Willuda et al. (2001) J. Biol. Chem. 276 (17) 14385-14392). Haemoglobin also has a tetramerisation domain that could be used for this kind of application. A multivalent TCR complex of the invention may have enhanced binding capability for the SLYNTVATL-HLA-A2 complex compared to a non-multimeric wild-type or T cell receptor heterodimer of the invention. Thus, multivalent complexes of TCRs of the invention are also included within the invention. Such multivalent TCR complexes according to the invention are particularly useful for tracking or targeting cells presenting particular antigens in vitro or in vivo, and are also useful as intermediates for the production of further multivalent TCR complexes having such uses.

As is well-known in the art, TCRs may be subject to post translational modifications. Glycosylation is one such modification, which comprises the covalent attachment of oligosaccharide moieties to defined amino acids in the TCR chain. For example, asparagine residues, or serine/threonine residues are well-known locations for oligosaccharide attachment. The glycosylation status of a particular protein depends on a number of factors, including protein sequence, protein conformation and the availability of certain enzymes. Furthermore, glycosylation status (i.e. oligosaccharide type, covalent linkage and total number of attachments) can influence protein function. Therefore, when producing recombinant proteins, controlling glycosylation is often desirable. Controlled glycosylation has been used to improve antibody based therapeutics. (Jefferis R., Nat Rev Drug Discov. 2009 March; 8(3):226-34). For soluble TCRs of the invention glycosylation may be controlled in vivo, by using particular cell lines for example, or in vitro, by chemical modification. Such modifications are desirable, since glycosylation can improve phamacokinetics, reduce immunogenicity and more closely mimic a native human protein (Sinclair A M and Elliott S., Pharm Sci. 2005 August; 94(8):1626-35).

For administration to patients, the TCRs of the invention (preferably associated with a detectable label or therapeutic agent or expressed on a transfected T cell) or cells of the invention may be provided in a pharmaceutical composition together with one or more pharmaceutically acceptable carriers or excipients. Therapeutic or imaging TCRs, or cells, in accordance with the invention will usually be supplied as part of a sterile, pharmaceutical composition which will normally include a pharmaceutically acceptable carrier. This pharmaceutical composition may be in any suitable form, (depending upon the desired method of administering it to a patient). It may be provided in unit dosage form, will generally be provided in a sealed container and may be provided as part of a kit. Such a kit would normally (although not necessarily) include instructions for use. It may include a plurality of said unit dosage forms.

The pharmaceutical composition may be adapted for administration by any appropriate route, such as parenteral (including subcutaneous, intramuscular, or intravenous), enteral (including oral or rectal), inhalation or intra-nasal routes. Such compositions may be prepared by any method known in the art of pharmacy, for example by mixing the active ingredient with the carrier(s) or excipient(s) under sterile conditions.

Dosages of the substances of the present invention can vary between wide limits, depending upon the disease or disorder to be treated, the age and condition of the individual to be treated, etc. a suitable dose range for a soluble TCR of the invention associated with an anti-CD3 antibody may be between 25 ng/kg and 50 μg/kg. A physician will ultimately determine appropriate dosages to be used.

TCRs, pharmaceutical compositions, vectors, nucleic acids and cells of the invention may be provided in substantially pure form, for example at least 80%, at least 85%, at least 90%, at least 91%, at least 92%, at least 93%, at least 94%, at least 95%, at least 96%, at least 97%, at least 98%, at least 99% or 100% pure.

Also provided by the invention are:

a TCR, nucleic acid or cell of the invention for use in medicine, preferably for use in a method of treating HIV infection or AIDS.

the use of a TCR, nucleic acid or cell of the invention in the manufacture of a medicament for treating HIV infection or AIDS;

a method of treating HIV infection in a patient, comprising administering to the patient a TCR, nucleic acid or cell of the invention.

Preferred features of each aspect of the invention are as for each of the other aspects *mutatis mutandis*. The prior art documents mentioned herein are incorporated to the fullest extent permitted by law.

DESCRIPTION OF FIGURES

FIG. 1 provides the amino acid sequence of the extracellular part of the alpha and beta chain of a wild type Gag TCR.

FIG. 2 provides the amino acid sequence of the soluble version of the wild type Gag TCR alpha and beta chain.

FIG. 3 provides amino acid sequences of mutated TCR alpha chain variable domains FIG. 4 provides amino acid sequence of mutated TCR beta chain variable domains FIG. 5 provides alpha chain amino acid sequences of TCR anti-CD3 fusion molecules.

FIG. 6 provides beta chain amino acid sequence of TCR anti-CD3 fusion molecules.

EXAMPLES

Example 1

Figure 7:
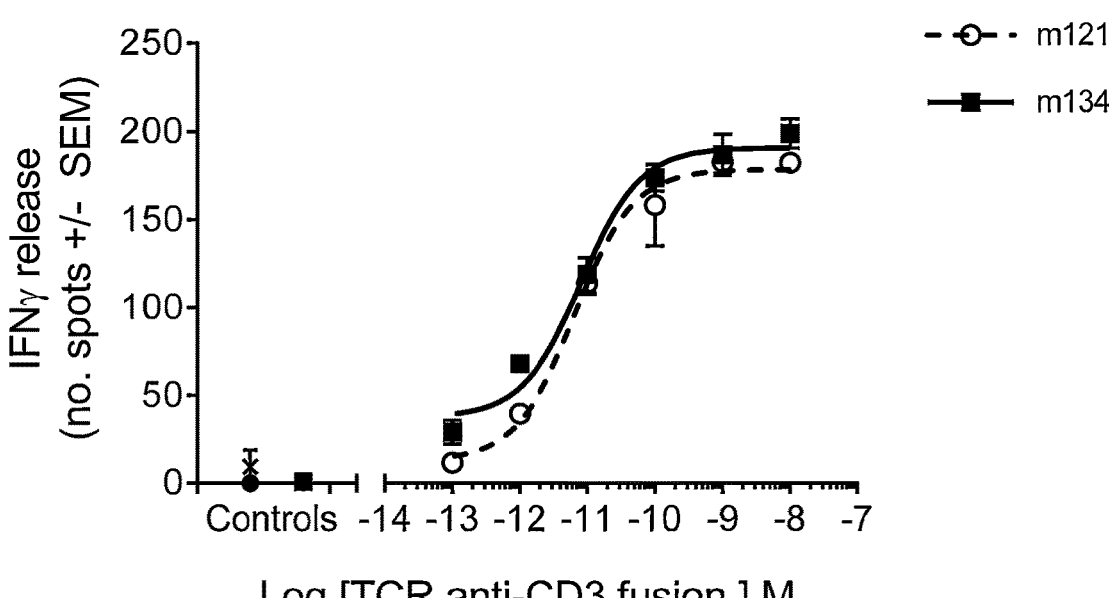
FIG. 7 provides cellular data demonstrating potency TCR anti-CD3 fusion molecules FIG. 8 provides cellular data demonstrating specificity of TCR anti-CD3 fusion molecules FIG. 9 provides cellular data demonstrating sensitivity of TCR anti-CD3 fusion molecules The invention is further described in the following non-limiting examples.

Expression, Refolding and Purification of Soluble TCRs

Method

DNA sequences encoding the alpha and beta extracellular regions of soluble TCRs of the invention were cloned separately into pGMT7-based expression plasmids using standard methods (as described in Sambrook, et al. *Molecular cloning. Vol.* 2. (1989) New York: Cold spring harbour laboratory press). The expression plasmids were transformed separately into *E. coli* strain Rosetta (BL21pLysS), and single ampicillin-resistant colonies were grown at 37° C. in TYP (+ampicillin 100 μg/ml) medium to an $OD_{600}$ of ~0.6-0.8 before inducing protein expression with 0.5 mM IPTG. Cells were harvested three hours post-induction by centrifugation. Cell pellets were lysed with BugBuster protein extraction reagent (Merck Millipore) according to the manufacturer's instructions. Inclusion body pellets were recovered by centrifugation. Pellets were washed twice in Triton buffer (50 mM Tris-HCl pH 8.1, 0.5% Triton-X100, 100 mM NaCl, 10 mM NaEDTA) and finally resuspended in detergent free buffer (50 mM Tris-HCl pH 8.1, 100 mM NaCl, 10 mM NaEDTA). Inclusion body protein yield was quantified by solubilising with 6 M guanidine-HCl and measuring $OD_{280}$. Protein concentration was then calculated using the extinction coefficient. Inclusion body purity was measured by solubilising with 8M Urea and loading ~2 μg onto 4-20% SDS-PAGE under reducing conditions. Purity was then estimated or calculated using densitometry software (Chemidoc, Biorad). Inclusion bodies were stored at +4° C. for short term storage and at −20° C. or −70° C. for longer term storage.

For soluble TCR refolding, α and β chain-containing inclusion bodies were first mixed and diluted into 10 ml solubilisation/denaturation buffer (6 M Guanidine-hydrochloride, 50 mM Tris HCl pH 8.1, 100 mM NaCl, 10 mM EDTA, 20 mM DTT) followed by incubation for 30 min at 37° C. Refolding was then initiated by further dilution into 1 L of refold buffer (100 mM Tris pH 8.1, 400 mM L-Arginine HCL, 2 mM EDTA, 4 M Urea, 10 mM cysteamine hydrochloride and 2.5 mM cystamine dihydrochloride) and the solution mixed well. The refolded mixture was dialysed against 10 L $H_2O$ for 18-20 hours at 5° C.±3° C. After this time, the dialysis buffer was twice replaced with 10 mM Tris pH 8.1 (10 L) and dialysis continued for another 15 hours. The refold mixture was then filtered through 0.45 μm cellulose filters.

Purification of soluble TCRs was initiated by applying the dialysed refold onto a POROS® 50HQ anion exchange column and eluting bound protein with a gradient of 0-500 mM NaCl in 20 mM Tris pH 8.1 over 50 column volumes using an Akta® purifier (GE Healthcare). Peak TCR fractions were identified by SDS PAGE before being pooled and concentrated. The concentrated sample was then applied to a Superdex® 75HR gel filtration column (GE Healthcare) pre-equilibrated in Dulbecco's PBS buffer. The peak TCR fractions were pooled and concentrated and the final yield of purified material calculated.

Example 2

Expression, Refolding and Purification of Soluble TCR Anti-CD3 Fusion Molecules Preparation of soluble TCR anti-CD3 fusions was carried out as described in Example 1, except that the TCR beta chain was fused via a linker to an anti-CD3 single chain antibody. In addition a cation exchange step was performed during purification following the anion exchange. In this case the peak fractions from anion exchange were diluted 20 fold in 20 mM MES (pH6.5), and applied to a POROS® 50HS cation exchange column. Bound protein was eluted with a gradient of 0-500 mM NaCl in 20 mM MES. Peak fractions were pooled and adjusted to 50 mM Tris pH 8.1, before being concentrated and applied directly to the gel filtration matrix as described in Example 1.

Example 3

Antigen Binding Characterisation of Soluble TCR Anti-CD3 Fusion Molecules

Binding analysis was carried out by surface plasmon resonance, using a BIAcore 3000 or BIAcore T200 instrument. Biotinylated class I HLA-A*02 molecules were refolded with the peptide of interest and purified using methods known to those in the art (O'Callaghan et al. (1999). Anal Biochem 266(1): 9-15; Garboczi, et al. (1992). Proc Natl Acad Sci USA 89(8): 3429-3433). Biotinylated peptide-HLA monomers were immobilized on to streptavidin-coupled CM-5 sensor chips. All measurements were performed at 25° C. in Dulbecco's PBS buffer, supplemented with 0.005% P20.

Equilibrium binding constants were determined using serial dilutions of soluble TCR/TCR anti-CD3 fusions injected at a constant flow rate of 30 ul min-1 over a flow cell coated with ~200 response units (RU) of peptide-HLA-A*02 complex. Equilibrium responses were normalised for each concentration by subtracting the bulk buffer response on a control flow cell containing an irrelevant peptide-HLA. The Kd value was obtained by non-linear curve fitting using Prism software and the Langmuir binding isotherm, bound=C*Max/(C+KD), where "bound" is the equilibrium binding in RU at injected TCR/TCR anti-CD3 concentration C and Max is the maximum binding.

For high affinity interactions, binding parameters were determined by single cycle kinetics analysis. Five different concentrations of TCR anti-CD3 fusion were injected over a flow cell coated with ~100-200 RU of peptide-HLA complex using a flow rate of 50-60 $\mu$l min-1. Typically, 60-200 $\mu$l of TCR anti-CD3 fusion was injected at a top concentration of 100-300 nM, with successive 2 fold dilutions used for the other four injections. The lowest concentration was injected first. To measure the dissociation phase buffer was then injected until ≥10% dissociation occurred, typically after 1-3 hours. Kinetic parameters were calculated using BIAevaluation® software. The dissociation phase was fitted to a single exponential decay equation enabling calculation of half-life. The equilibrium constant Kd was calculated from koff/kon.

Results

The binding parameters (dissociation constant (Kd) and half-life (T½)) of two mutant TCRs of the invention fused to anti-CD3 are shown in the table below. The Kd value of a soluble form of the none mutated TCR, without anti-CD3, was previously determined as 85 nM (WO2006103429 and Varela-Rohena et al. 2008, Nat Med, 14(12)1390-5).

| TCR-anti-CD3 fusion | Alpha chain variable sequence | Beta chain variable sequences | Kd | T½ |
|---|---|---|---|---|
| m121 | SEQ ID NO: 9 (with Q at position 1 and the optional 8 residues present at the C terminus of TRAC) | SEQ ID No: 11 | 64 pM | 94 h |
| m134 | SEQ ID NO: 10 (with Q at position 1 and the optional 8 residues present at the C terminus of TRAC) | SEQ ID No: 11 | 193 pM | 16.6 h |

COMPARATIVE EXAMPLE

The previously known highest affinity mutant of the WT TCR (termed a11b6, (Varela-Rohena et al. 2008, Nat Med, 14(12):1390-5)) was prepared as an anti-CD3 fusion and assessed for binding under the same conditions as m121 and m134 above. In this case the binding affinity (Kd) was calculated as 360 pM and the half-life was 3.5 h.

These results demonstrate that mutant TCRs of the invention have unexpectedly high affinity and long binding half-life for the SLYNTVATL-HLA-A*02 complex, compared to the WT TCR, and other previously disclosed high affinity variants, making them particularly suitable for use as soluble therapeutic agents for redirecting a T cell response against HIV infected cells presenting low levels of SLYNTVATL-HLA-A*02 complex.

Example 4

Potent T Cell Redirection Against Cells Presenting SLYNTVATL-HLA-a*02 Complex by TCR Anti-CD3 Fusion Molecules The ability of the TCR anti-CD3 fusions of the invention to drive a potent T cell response in the presence of cells presenting the SLYNTVATL-HLA-A*02 complex was investigated using an ELISPOT assay, with IFNγ secretion as a read out for T cell activation.

Assays were carried out using the IFNγ ELISPOT assay kit (BD Biosciences, cat no 551849), as directed by the manufacturer. T2 cells (American Type Culture Collection) pulsed with 1 nM SLYNTVATL peptide were used as target cells, and plated at 5×10⁴ cells/well in 50 $\mu$l. Titrated concentrations of TCR-anti CD3 fusions were then added at final concentrations of 10, 1, 0.1, 0.01, 0.001, 0.0001 nM in 50 $\mu$l. Effector cells (CD8+ T cells) from donor PBMCs were isolated by Ficoll-Hypaque density gradient separation (Lymphoprep, Nycomed Pharma AS), utilising Lymphoprep (Axis-Shields, cat no NYC-1114547) and Leucosep tubes (Greiner, cat no 227290). CD8+ T cells were enriched from PBMC by negative selections using magnetic bead immunodepletion, in accordance with the manufacturer's instructions (MACS, Miltenyi Biotec). Effector cells were plated at 8×10⁴ cells/well in 50 $\mu$l. The final volume of each well was made up to 200 $\mu$l with assay buffer (10% FCS, 88% RPMI, 1% glutamine, 1% penicillin/streptomycin).

Plates were incubated for 18-20 h at 37° C. and 5% $CO_2$ and quantified after development using an automated ELISpot reader (Immunospot Series 5 Analyzer, Cellular Technology Ltd).

Target cells presenting an irrelevant peptide were added as a negative control in the presence of effectors and 1 nM TCR-anti CD3 fusion. Additional control samples were prepared with effectors cell plus target cells and effectors alone. Data were analysed using Prism 5.0 software (Graph Pad, Software) to calculate EC50 values Results FIG. 7 shows the response curves produced by m121 and m134. The $EC_{50}$ values derived from the curves are in the table below

| TCR ID | Alpha chain variable sequence | Beta chain variable sequence | $EC_{50}$ (pM) |
|---|---|---|---|
| m121 | SEQ ID NO: 9 (with Q at position 1 and the optional 8 residues present at the C terminus of TRAC) | SEQ ID NO: 11 | 6 |

-continued

| TCR ID | Alpha chain variable sequence | Beta chain variable sequence | EC$_{50}$ (pM) |
|---|---|---|---|
| m134 | SEQ ID NO: 10 (with Q at position 1 and the optional 8 residues present at the C terminus of TRAC) | SEQ ID NO: 11 | 8 |

COMPARATIVE EXAMPLE

The previously known highest affinity mutant of the WT TCR (termed a11b6, (Varela-Rohena et al. 2008, Nat Med, 14(12):1390-5)) was prepared as an anti-CD3 fusion and the EC$_{50}$ value determined at the same time and under identical conditions as for m121 and m134 above. The EC$_{50}$ value for a11b6 was calculated to be 135 pM.

These data demonstrate that the TCR-anti CD3 fusions of the invention are, unexpectedly, highly potent at redirecting T cells against cells presenting SLYNTVATL-HLA-A*02 complex, and are therefore ideal as therapeutic reagents for targeting HIV infected cells presenting low levels of SLYN-TVATL-HLA-A*02 complex.

Example 5

Specific T Cell Redirection by TCR Anti-CD3 Fusions

Figure 8:
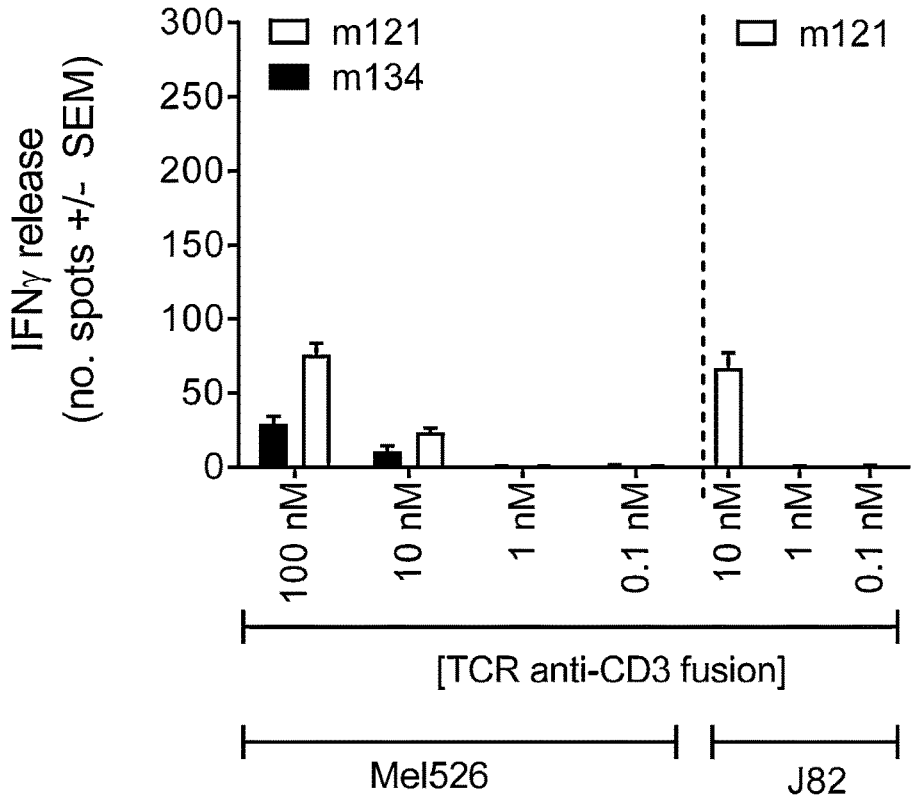

The specificity of TCR-anti CD3 fusions was assessed by IFNγ ELISPOT assay using antigen-negative, HLA-A*02-positive, human cancer cell lines as target cells (melanoma cells MeI526 (Thymed) and bladder cancer cells J82 (American Type Culture Collection)). The assays were carried out using the same procedure as described in Example 4. Various concentrations of TCR anti-CD3 fusions were used as indicated in FIG. 8.
Results The data presented in FIG. 8 indicate that low-levels of non-specific T cell activation could only be detected at high concentrations of TCR-anti CD3 fusions, i.e. at least 1000-fold greater than EC50 values, and outside of the expected therapeutic range (greater than 10$^{-9}$M). Therefore the TCRs of the invention have an unexpectedly high level of target specificity.

Example 6

Figure 9:
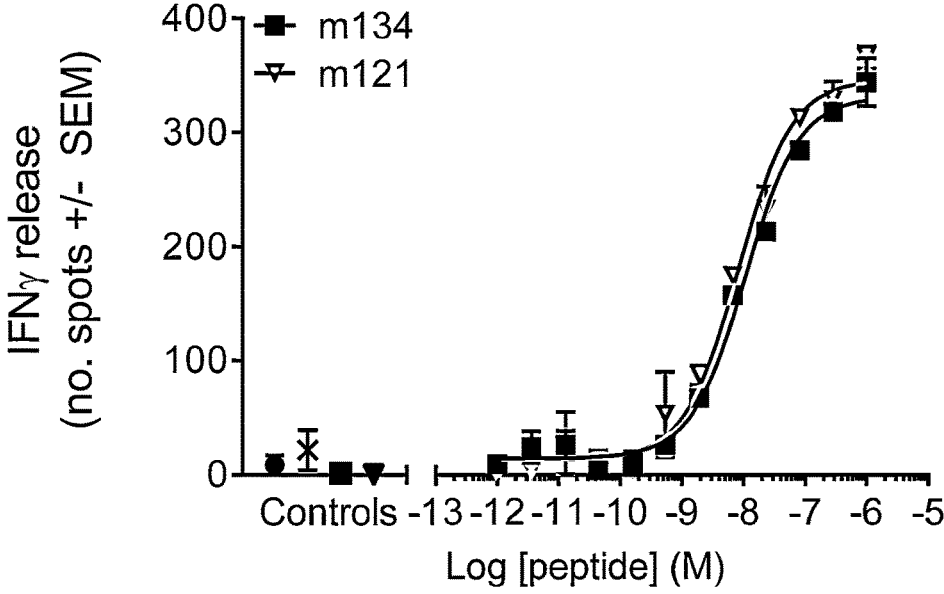

T Cell Redirection by TCR Anti-CD3 Fusions Occurs Even at Low Peptide Concentrations To determine the sensitivity of TCR anti-CD3 fusions of the invention to peptide HLA-complex, peptide titration experiments were carried out using T2 cells pulsed with various concentrations of peptide. T cell activation was determined using the same IFNγ ELISPOT procedure as described in Example 4. TCR anti-CD3 fusions were used at a concentration of 1 nM. Peptide concentrations are indicated in FIG. 9.
Results The data presented in FIG. 9 demonstrate that TCR anti-CD3 fusions are sensitive to low nanomolar concentrations of exogenously loaded peptide. It has been shown in the art that pulsing T2 cells at peptide concentrations of 10-9 M results in low number of epitopes per cell (>50) and corresponds to the number of epitopes presented on the surface of cancer cells (Bossi et al. Oncoimmunology, 2013, 2(11): e26840); therefore, the TCRs of the invention are unexpectedly highly sensitive to cells presenting very low number of epitopes. Such a high level of sensitivity may facilitate the clearance of reservoirs of virally infected cells in vivo.

SEQUENCE LISTING

```
Sequence total quantity: 38
SEQ ID NO: 1            moltype = AA  length = 9
FEATURE                 Location/Qualifiers
source                  1..9
                        mol_type = protein
                        organism = Homo sapiens
SEQUENCE: 1
SLYNTVATL                                                     9

SEQ ID NO: 2            moltype = AA  length = 206
FEATURE                 Location/Qualifiers
source                  1..206
                        mol_type = protein
                        organism = Homo sapiens
SEQUENCE: 2
MQKEVEQNSG PLSVPEGAIA SLNCTYSDRG SQSFFWYRQY SGKSPELIMF IYSNGDKEDG  60
RFTAQLNKAS QYISLLIRDS KLSDSATYLC AVRTNSGYAL NFGKGTSLLV TPHIQKPDPA  120
VYQLRDSKSS DKSVCLFTDF DSQTNVSQSK DSDVYITDKT VLDMRSMDFK SNSAVAWSNK  180
SDFACANAFN NSIIPEDTFF PSPESS                                    206

SEQ ID NO: 3            moltype = AA  length = 243
FEATURE                 Location/Qualifiers
source                  1..243
                        mol_type = protein
                        organism = Homo sapiens
SEQUENCE: 3
MDAGVTQSPT HLIKTRGQQV TLRCSPKSGH DTVSWYQQAL GQGPQFIFQY YEEEERQRGN  60
FPDRFSGHQF PNYSSELNVN ALLLGDSALY LCASSDTVSY EQYFGPGTRL TVTEDLKNVF  120
PPEVAVFEPS EAEISHTQKA TLVCLATGFY PDHVELSWWV NGKEVHSGVS TDPQPLKEQP  180
ALNDSRYCLS SRLRVSATFW QNPRNHFRCQ VQFYGLSEND EWTQDRAKPV TQIVSAEAWG  240
```

-continued

```
RAD                                                                 243

SEQ ID NO: 4              moltype = AA  length = 206
FEATURE                   Location/Qualifiers
source                    1..206
                          mol_type = protein
                          organism = Homo sapiens
SEQUENCE: 4
MQKEVEQNSG PLSVPEGAIA SLNCTYSDRG SQSFFWYRQY SGKSPELIMF IYSNGDKEDG  60
RFTAQLNKAS QYISLLIRDS KLSDSATYLC AVRTNSGYAL NFGKGTSLLV TPHIQKPDPA  120
VYQLRDSKSS DKSVCLFTDF DSQTNVSQSK DSDVYITDKC VLDMRSMDFK SNSAVAWSNK  180
SDFACANAFN NSIIPEDTFF PSPESS                                       206

SEQ ID NO: 5              moltype = AA  length = 243
FEATURE                   Location/Qualifiers
source                    1..243
                          mol_type = protein
                          organism = Homo sapiens
SEQUENCE: 5
MDAGVTQSPT HLIKTRGQQV TLRCSPKSGH DTVSWYQQAL GQGPQFIFQY YEEEERQRGN  60
FPDRFSGHQF PNYSSELNVN ALLLGDSALY LCASSDTVSY EQYFGPGTRL TVTEDLKNVF  120
PPEVAVFEPS EAEISHTQKA TLVCLATGFY PDHVELSWWV NGKEVHSGVC TDPQPLKEQP  180
ALNDSRYALS SRLRVSATFW QDPRNHFRCQ VQFYGLSEND EWTQDRAKPV TQIVSAEAWG  240
RAD                                                                 243

SEQ ID NO: 6              moltype = AA  length = 111
FEATURE                   Location/Qualifiers
REGION                    1..111
                          note = a15 m121
source                    1..111
                          mol_type = protein
                          organism = synthetic construct
SEQUENCE: 6
QKEVEQNSGP LSVPEGAIAS LNCTYSSWEG QSFFWYRQYS GKSPELIMFL YADPDKEDGR  60
FTAQLNKASQ YISLLIRDSK LSDSATYLCA VRTNSGYALN FGKGTSLLVT P           111

SEQ ID NO: 7              moltype = AA  length = 111
FEATURE                   Location/Qualifiers
REGION                    1..111
                          note = a12 m134
source                    1..111
                          mol_type = protein
                          organism = synthetic construct
SEQUENCE: 7
QKEVEQNSGP LSVPEGAIAS LNCTYSSWEG QSFFWYRQYS GKSPELIMFI YSNGDKEDGR  60
FTAQLNKASQ YISLLIRDSK LSDSATYLCA VRTNSGYALN FGKGTSLLVT P           111

SEQ ID NO: 8              moltype = AA  length = 112
FEATURE                   Location/Qualifiers
REGION                    1..112
                          note = b26 m121 and m134
source                    1..112
                          mol_type = protein
                          organism = synthetic construct
SEQUENCE: 8
DAGVTQSPTH LIKTRGQQVT LRCSPKSGHD TVSWYQQALG QGPQFIFQAV RGVERQRGNF  60
PDRFSGHQFP NYSSELNVNA LLLGDSALYL CASSDTVSYE QYFGPGTRLT VT          112

SEQ ID NO: 9              moltype = AA  length = 206
FEATURE                   Location/Qualifiers
REGION                    1..206
                          note = m121: Alpha chain (comprising SEQ ID NO: 6 and the
                           constant domain of SEQ ID NO: 4, the last 8 amino acids at
                           the C terminus are optional).
VARIANT                   1
                          note = X can be either A or Q
REGION                    199..206
                          note = OPTIONAL - The last 8 amino acids at the C terminus
                           are optional
source                    1..206
                          mol_type = protein
                          organism = synthetic construct
SEQUENCE: 9
XKEVEQNSGP LSVPEGAIAS LNCTYSSWEG QSFFWYRQYS GKSPELIMFL YADPDKEDGR  60
FTAQLNKASQ YISLLIRDSK LSDSATYLCA VRTNSGYALN FGKGTSLLVT PHIQKNPDPA  120
VYQLRDSKSS DKSVCLFTDF DSQTNVSQSK DSDVYITDKC VLDMRSMDFK SNSAVAWSNK  180
SDFACANAFN NSIIPEDTFF PSPESS                                       206

SEQ ID NO: 10             moltype = AA  length = 206
```

-continued

```
FEATURE              Location/Qualifiers
REGION               1..206
                     note = m134: Alpha chain (comprising SEQ ID NO: 7 and the
                      constant domain of SEQ ID NO: 4, the last 8 amino acids at
                      the C terminus are optional)
VARIANT              1
                     note = X can be either A or Q
REGION               199..206
                     note = OPIONAL - The last 8 amino acids at the C terminus
                      are optional
source               1..206
                     mol_type = protein
                     organism = synthetic construct
SEQUENCE: 10
XKEVEQNSGP LSVPEGAIAS LNCTYSSWEG QSFFWYRQYS GKSPELIMFI YSNGDKEDGR   60
FTAQLNKASQ YISLLIRDSK LSDSATYLCA VRTNSGYALN FGKGTSLLVT PHIQKNPDPA  120
VYQLRDSKSS DKSVCLFTDF DSQTNVSQSK DSDVYITDKC VLDMRSMDFK SNSAVAWSNK  180
SDFACANAFN NSIIPEDTFF PSPESS                                       206

SEQ ID NO: 11         moltype = AA  length = 500
FEATURE              Location/Qualifiers
REGION               1..500
                     note = Beta chain (comprising an anti-CD3 scFv (grey) fused
                      via a linker (italics) to a TCR beta chain comprising SEQ
                      ID NO: 8 and the constant domain of SEQ ID NO: 5)
source               1..500
                     mol_type = protein
                     organism = synthetic construct
SEQUENCE: 11
AIQMTQSPSS LSASVGDRVT ITCRASQDIR NYLNWYQQKP GKAPKLLIYY TSRLESGVPS   60
RFSGSGSGTD YTLTISSLQP EDFATYYCQQ GNTLPWTFGQ GTKVEIKGGG GSGGGGSGGG  120
GSGGGGSGGG SEVQLVESGG GLVQPGGSLR LSCAASGYSF TGYTMNWVRQ APGKGLEWVA  180
LINPYKGVST YNQKFKDRFT ISVDKSKNTA YLQMNSLRAE DTAVYYCARS GYYGDSDWYF  240
DVWGQGTLVT VSSGGGGSDA GVTQSPTHLI KTRGQQVTLR CSPKSGHDTV SWYQQALGQG  300
PQFIFQAVRG VERQRGNFPD RFSGHQFPNY SSELNVNALL LGDSALYLCA SSDTVSYEQY  360
FGPGTRLTVT EDLKNVFPPE VAVFEPSEAE ISHTQKATLV CLATGFYPDH VELSWWVNGK  420
EVHSGVCTDP QPLKEQPALN DSRYALSSRL RVSATFWQDP RNHFRCQVQF YGLSENDEWT  480
QDRAKPVTQI VSAEAWGRAD                                              500

SEQ ID NO: 12         moltype = AA  length = 5
FEATURE              Location/Qualifiers
REGION               1..5
                     note = Linker
source               1..5
                     mol_type = protein
                     organism = synthetic construct
SEQUENCE: 12
GGGGS                                                                5

SEQ ID NO: 13         moltype = AA  length = 5
FEATURE              Location/Qualifiers
REGION               1..5
                     note = Linker
source               1..5
                     mol_type = protein
                     organism = synthetic construct
SEQUENCE: 13
GGGSG                                                                5

SEQ ID NO: 14         moltype = AA  length = 5
FEATURE              Location/Qualifiers
REGION               1..5
                     note = Linker
source               1..5
                     mol_type = protein
                     organism = synthetic construct
SEQUENCE: 14
GGSGG                                                                5

SEQ ID NO: 15         moltype = AA  length = 5
FEATURE              Location/Qualifiers
REGION               1..5
                     note = Linker
source               1..5
                     mol_type = protein
                     organism = synthetic construct
SEQUENCE: 15
GSGGG                                                                5
```

```
SEQ ID NO: 16        moltype = AA   length = 6
FEATURE              Location/Qualifiers
REGION               1..6
                     note = Linker
source               1..6
                     mol_type = protein
                     organism = synthetic construct
SEQUENCE: 16
GSGGGP                                                           6

SEQ ID NO: 17        moltype = AA   length = 5
FEATURE              Location/Qualifiers
REGION               1..5
                     note = Linker
source               1..5
                     mol_type = protein
                     organism = synthetic construct
SEQUENCE: 17
GGEPS                                                            5

SEQ ID NO: 18        moltype = AA   length = 7
FEATURE              Location/Qualifiers
REGION               1..7
                     note = Linker
source               1..7
                     mol_type = protein
                     organism = synthetic construct
SEQUENCE: 18
GGEGGGP                                                          7

SEQ ID NO: 19        moltype = AA   length = 12
FEATURE              Location/Qualifiers
REGION               1..12
                     note = Linker
source               1..12
                     mol_type = protein
                     organism = synthetic construct
SEQUENCE: 19
GGEGGGSEGG GS                                                    12

SEQ ID NO: 20        moltype = AA   length = 6
FEATURE              Location/Qualifiers
source               1..6
                     mol_type = protein
                     organism = Homo sapiens
SEQUENCE: 20
DRGSQS                                                           6

SEQ ID NO: 21        moltype = AA   length = 6
FEATURE              Location/Qualifiers
source               1..6
                     mol_type = protein
                     organism = Homo sapiens
SEQUENCE: 21
IYSNGD                                                           6

SEQ ID NO: 22        moltype = AA   length = 11
FEATURE              Location/Qualifiers
source               1..11
                     mol_type = protein
                     organism = Homo sapiens
SEQUENCE: 22
AVRTNSGYAL N                                                     11

SEQ ID NO: 23        moltype = AA   length = 6
FEATURE              Location/Qualifiers
source               1..6
                     mol_type = protein
                     organism = Homo sapiens
SEQUENCE: 23
SGHDTV                                                           6

SEQ ID NO: 24        moltype = AA   length = 6
FEATURE              Location/Qualifiers
source               1..6
                     mol_type = protein
                     organism = Homo sapiens
SEQUENCE: 24
YYEEE                                                            6
```

-continued

```
SEQ ID NO: 25           moltype = AA   length = 11
FEATURE                 Location/Qualifiers
source                  1..11
                        mol_type = protein
                        organism = Homo sapiens

SEQUENCE: 25
ASSDTVSYEQ Y                                                    11

SEQ ID NO: 26           moltype = AA   length = 6
FEATURE                 Location/Qualifiers
REGION                  1..6
                        note = a15 m121 CDR
source                  1..6
                        mol_type = protein
                        organism = synthetic construct

SEQUENCE: 26
SWEGQS                                                          6

SEQ ID NO: 27           moltype = AA   length = 6
FEATURE                 Location/Qualifiers
REGION                  1..6
                        note = a15 m121 CDR
source                  1..6
                        mol_type = protein
                        organism = synthetic construct

SEQUENCE: 27
LYADPD                                                          6

SEQ ID NO: 28           moltype = AA   length = 6
FEATURE                 Location/Qualifiers
REGION                  1..6
                        note = b26 m121 and m134 CDR
source                  1..6
                        mol_type = protein
                        organism = synthetic construct

SEQUENCE: 28
AVRGVE                                                          6

SEQ ID NO: 29           moltype = AA   length = 9
FEATURE                 Location/Qualifiers
source                  1..9
                        mol_type = protein
                        organism = Homo sapiens

SEQUENCE: 29
SLFNTVATL                                                       9

SEQ ID NO: 30           moltype = AA   length = 9
FEATURE                 Location/Qualifiers
source                  1..9
                        mol_type = protein
                        organism = Homo sapiens

SEQUENCE: 30
SLFNTVAVL                                                       9

SEQ ID NO: 31           moltype = AA   length = 9
FEATURE                 Location/Qualifiers
source                  1..9
                        mol_type = protein
                        organism = Homo sapiens

SEQUENCE: 31
SLSNTVATL                                                       9

SEQ ID NO: 32           moltype = AA   length = 9
FEATURE                 Location/Qualifiers
source                  1..9
                        mol_type = protein
                        organism = Homo sapiens

SEQUENCE: 32
SSFNTVATL                                                       9

SEQ ID NO: 33           moltype = AA   length = 9
FEATURE                 Location/Qualifiers
source                  1..9
                        mol_type = protein
                        organism = Homo sapiens SEQUENCE: 33
SLLNTVATL                                                       9
```

-continued

```
SEQ ID NO: 34          moltype = AA  length = 9
FEATURE                Location/Qualifiers
source                 1..9
                       mol_type = protein
                       organism = Homo sapiens
SEQUENCE: 34
SLYNTIATL                                                         9

SEQ ID NO: 35          moltype = AA  length = 9
FEATURE                Location/Qualifiers
source                 1..9
                       mol_type = protein
                       organism = Homo sapiens
SEQUENCE: 35
SLYNTIAVL                                                         9

SEQ ID NO: 36          moltype = AA  length = 9
FEATURE                Location/Qualifiers
source                 1..9
                       mol_type = protein
                       organism = Homo sapiens
SEQUENCE: 36
SLFNTIATL                                                         9

SEQ ID NO: 37          moltype = AA  length = 9
FEATURE                Location/Qualifiers
source                 1..9
                       mol_type = protein
                       organism = Homo sapiens
SEQUENCE: 37
SLFNTIAVL                                                         9

SEQ ID NO: 38          moltype = AA  length = 9
FEATURE                Location/Qualifiers
source                 1..9
                       mol_type = protein
                       organism = Homo sapiens
SEQUENCE: 38
SLFNFVATL                                                         9
```

The invention claimed is:

1. A soluble T cell receptor (TCR)-anti-CD3 fusion molecule that specifically binds to SLYNTVATL (SEQ ID NO: 1) in complex with HLA-A*02 comprising a TCR alpha chain comprising a TCR alpha chain variable domain and a TCR beta chain comprising a TCR beta chain variable domain, wherein (i) the TCR alpha chain variable domain comprises an amino acid sequence comprising at least 94% sequence identity to SEQ ID NO: 6; and (ii) the TCR beta chain variable domain comprises an amino acid sequence comprising the sequence of SEQ ID NO: 8;

wherein an anti-CD3 antibody is covalently linked to the N-terminus or the C-terminus of the TCR beta chain.

2. The soluble TCR-anti-CD3 fusion molecule of claim 1, wherein the TCR alpha chain variable domain comprises a CDR1 sequence of SEQ ID NO: 26 and a CDR2 sequence of SEQ ID NO: 27.

3. The soluble TCR-anti-CD3 fusion molecule of claim 2, wherein the TCR beta chain variable domain comprises a CDR1 sequence of SEQ ID NO: 23, a CDR2 sequence of SEQ ID NO: 28, and a CDR3 sequence of SEQ ID NO: 25.

4. The soluble TCR-anti-CD3 fusion molecule of claim 1, which is an alpha-beta heterodimer, having a TCR alpha chain TRAC constant domain sequence and a TCR beta chain TRBC1 or TRBC2 constant domain sequence, optionally wherein the TCR alpha and beta chain constant domain sequences are modified by truncation or substitution to delete the native disulfide bond between Cys4 of exon 2 of TRAC and Cys2 of exon 2 of TRBC 1 or TRBC2, wherein the TCR alpha and beta chain constant domain sequence(s) are modified by substitution of cysteine residues for Thr 48 of TRAC and Ser 57 of TRBC1 or TRBC2, the said cysteines forming a disulfide bond between the TCR alpha and beta constant domains of the soluble TCR-anti-CD3 fusion molecule.

5. The soluble TCR-anti-CD3 fusion molecule of claim 1, comprising a TCR in single chain format of the type Va-L-Vb, Vb-L-Va, Va-Ca-L-Vb, Va-L-Vb-Cb, Va-Ca-L-Vb-Cb, or Vb-Cb-L-Va-Ca, wherein Va and Vb are TCR alpha and beta variable regions respectively, Ca and Cb are TCR alpha and beta constant regions respectively, and L is a linker sequence.

6. The soluble TCR-anti-CD3 fusion molecule of claim 1, wherein the anti-CD3 antibody is covalently linked via a linker sequence selected from the group consisting of GGGGS (SEQ ID NO: 12), GGGSG (SEQ ID NO: 13), GGSGG (SEQ ID NO: 14), GSGGG (SEQ ID NO: 15), GSGGGP (SEQ ID NO: 16), GGEPS (SEQ ID NO: 17), GGEGGGP (SEQ ID NO: 18), and GGEGGGSEGGGS (SEQ ID NO: 19).

* * * * *